US006964847B1

(12) United States Patent  
Englert

(10) Patent No.: US 6,964,847 B1
(45) Date of Patent: Nov. 15, 2005

(54) DERIVATIVE NUCLEIC ACIDS AND USES THEREOF

(75) Inventor: David F. Englert, West Hartford, CT (US)

(73) Assignee: Packard Biosciences Company, Meriden, CT (US)

( * ) Notice: Subject to any disclaimer, the term of this patent is extended or adjusted under 35 U.S.C. 154(b) by 0 days.

(21) Appl. No.: 09/616,787

(22) Filed: Jul. 14, 2000

Related U.S. Application Data

(60) Provisional application No. 60/143,804, filed on Jul. 14, 1999.

(51) Int. Cl.[7] .......................... C12Q 1/68; C12N 15/00; C12N 15/63; C12N 1/20; C07H 21/04
(52) U.S. Cl. ...................... 435/6; 435/302.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2; 536/24.3, 23.1, 32, 33; 935/6; 436/518

(56) References Cited

U.S. PATENT DOCUMENTS

| | | | |
|---|---|---|---|
| 5,104,792 A | 4/1992 | Silver et al. | |
| 5,422,252 A | 6/1995 | Walker et al. | 435/91.2 |
| 5,445,934 A | 8/1995 | Fodor et al. | |
| 5,503,980 A | 4/1996 | Cantor | 435/6 |
| 5,508,169 A | 4/1996 | Deugau et al. | |
| 5,552,270 A | 9/1996 | Khrapko et al. | |
| 5,631,134 A | 5/1997 | Cantor | |
| 5,700,637 A | 12/1997 | Southern | |
| 5,714,320 A | 2/1998 | Kool | |
| 5,770,365 A | 6/1998 | Lane et al. | |
| 5,846,717 A | 12/1998 | Brow et al. | 435/6 |
| 5,858,989 A | 1/1999 | Babiuk et al. | 514/44 |
| 5,871,911 A | 2/1999 | Dahlberg et al. | |
| 5,876,924 A | 3/1999 | Zhang et al. | 435/5 |
| 5,888,780 A | 3/1999 | Dahlberg et al. | 435/91.53 |
| 5,935,793 A | 8/1999 | Wong | 435/6 |
| 5,942,391 A * | 8/1999 | Zhang et al. | 435/6 |
| 5,985,557 A | 11/1999 | Prudent et al. | 435/6 |
| 5,994,069 A | 11/1999 | Hall et al. | 435/6 |
| 6,001,567 A | 12/1999 | Brow et al. | 435/6 |
| 6,103,474 A * | 8/2000 | Dellinger | 435/6 |
| 6,255,081 B1 * | 7/2001 | Matsui | 435/91.1 |
| 6,261,797 B1 * | 7/2001 | Sorge | 435/41 |

FOREIGN PATENT DOCUMENTS

| | | |
|---|---|---|
| EP | 0373203 B1 | 8/1994 |
| WO | WO 96/15271 | 5/1996 |
| WO | WO 97/45559 | 12/1997 |
| WO | WO 98/35058 | 8/1998 |

OTHER PUBLICATIONS

Broude et al., "Enhanced DNA Sequencing by Hybridization", Proc. Natl. Acad. Sci. USA, vol. 91, pp. 3072–3076, 1994.

Pastinen et al., "Minisequencing: A Specific Tool for DNA Analysis and Diagnostics on Oligonucleotide Arrays", Genome Research, 7:606–614, 1997.
Brownie et al., "The Elimination of Primer–Dimer Accumulation in PCR", Nucleic Acids Research, vol. 25, No. 16, pp. 3235–3241, 1997.
Bukanov et al., "PD–loop: A complex of duplex DNA with an oligonucleotide", Proc. Natl. Acad. Sci. USA 95:5516–5520 (1998).
Cargill et al., "Characterization of single–nucleotide polymorphisms in coding regions of human genes", Nature Genetics 22:231–238 (1999).
Drobyshev et al., "Sequence analysis by hybridization with oligonucleotide microchip: indentification of β–thalassemia mutations", Gene 188:45–52 (1997).
Dubiley et al., "Fractionation, phosphorylation and ligation on oligonucleotide microchips to enhance sequencing by hybridization", Nucl. Acids Res. 25:2259–2265 (1997).
Favis et al., "Universal DNA array detection of small insertions and deletions in BRCA1 and BRCA2", Nature Biotechnology 18:561–564 (2000).
Griffin et al., "Direct genetic analysis by matrix–assisted laser desorption/ionization mass spectrometry", Proc. Natl. Acad. Sci. USA 96:6301–6306 (1999).
Gunderson et al., "Mutation Detection by Ligation to Complete n–mer DNA Arrays", Genome Research 8:1142–1153 (1998).
Isaksson and Landegren, "Accessing genomic information: alternatives to PCR", Current Opinion in Biotechnology 10:11–15 (1999).
Kuhn et al., "An Experimental Study of Mechanism and Specificity of Peptide Nucleic Acid (PNA) Binding to Duplex DNA", J. Mol. Biol.286:1337–1345 (1999).
Livshits and Mirzabekov, "Theoretical Analysis of the Kinetics of DNA Hybridization with Gel–Immobilized Oligonucleotides", Biophysical Journal 71:2795–2801 (1996).
Mir and Southern, "Determining the influence of structure on hybridization using oligonucleotide arrays", Nature Biotechnology 17:788–792 (1999).
Ryan et al, "Non–PCR–Dependent Detection of the Factor V Leiden Mutation From Genomic DNA Using a Homogeneous Invader Microtiter Plate Assay", Molecular Diagnosis 4:135–144 (1999).
Thomas et al., "Amplification of Padlock Probes for DNA Diagnostics by Cascade Rolling Circle Amplification or the Polymerase Chain Reaction", Arch Pathol Lab Med 123:1170–1176 (1999).
Timofeev et al., "Regioselective immobilization of short oligonucleotides to acrylic copolymer gels", Nucl. Acids Res. 24:3142–3148 (1996).

(Continued)

Primary Examiner—Jeffrey Fredman
Assistant Examiner—Arun Chakrabarti
(74) Attorney, Agent, or Firm—Fish & Richardson P.C.

(57) ABSTRACT

The invention features a method for multiplexed analysis of a plurality of target nucleic acid sequences in a sample. The method provides a derivative nucleic acid for each target sequence analyzed and present in the sample.

19 Claims, 10 Drawing Sheets

OTHER PUBLICATIONS

Wang et al., "Large–Scale Identification, Mapping, and Genotyping of Single–Nucleotide Polymorphisms in the Human Genome", *Science 280*:1077–1082 (1998).

Yershov et al., "DNA analysis and diagnostics on oligonucleotide microchips", *Proc. Natl. Acad. USA 93*:4913–4918 (1996).

Zhang et al., "Amplification of target–specific, ligation–dependent circular probe", *Gene 211*:277–285 (1998).

Newton and Graham: "PCR" 1994, Spektrum Akademischer Verlag, Heidelberg, XP002299813, p. 70–71, Figure 4.1.

Supplemental European Search Report for EP Application No. 00 95 0341, dated Oct. 8, 2004.

* cited by examiner

1) PCR with low concentrations of target-specific primer/adapters
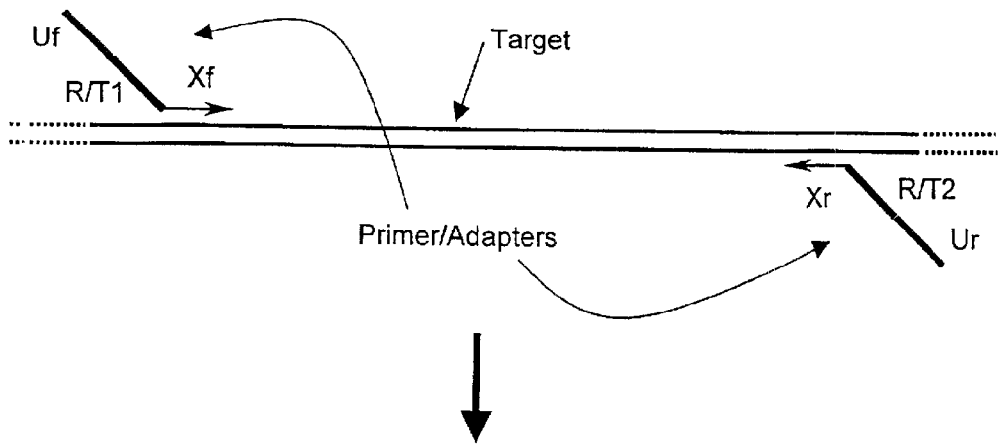
2) PCR with high concentrations of universal primers
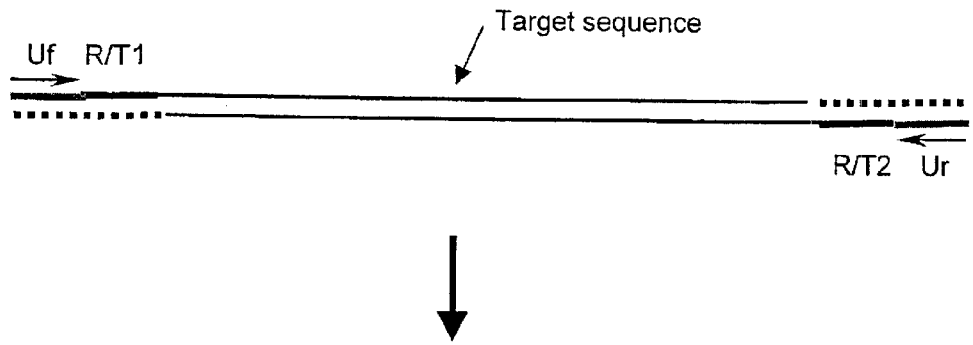
FIG. 2
(1 OF 3)

3) Digest with restriction enzyme, leaving tag sequences in the 3' overhangs at the ends of the target sequence
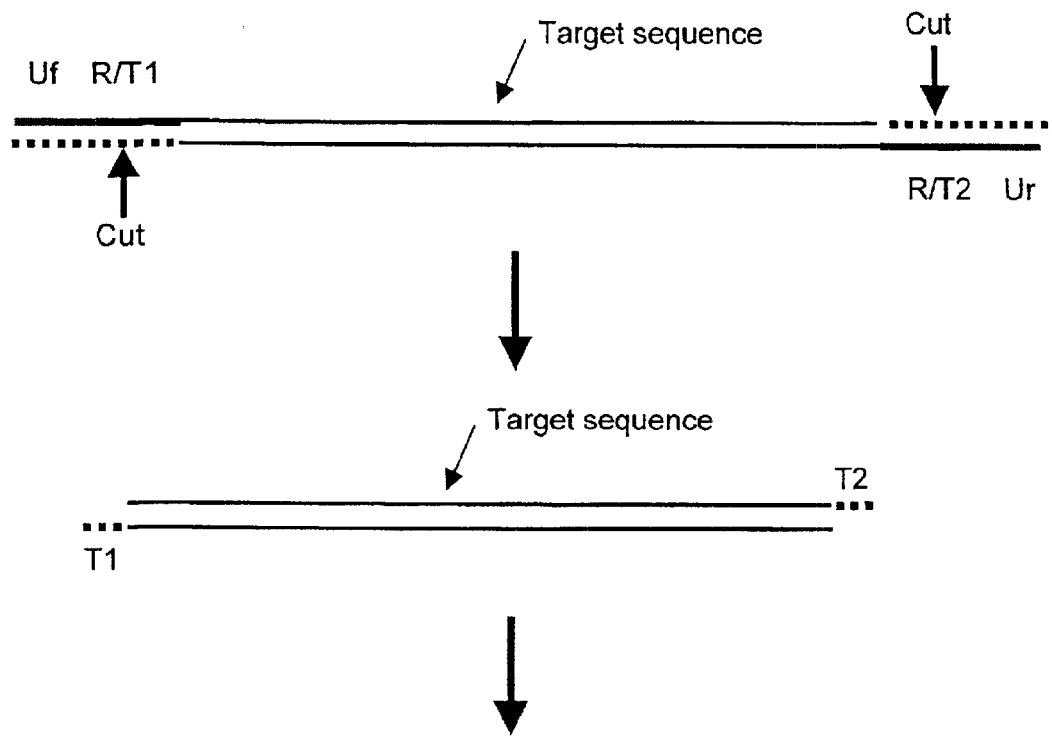
4) Capture target sequence on either or both of two partially duplex probes, complementary to tags T1 or T2.
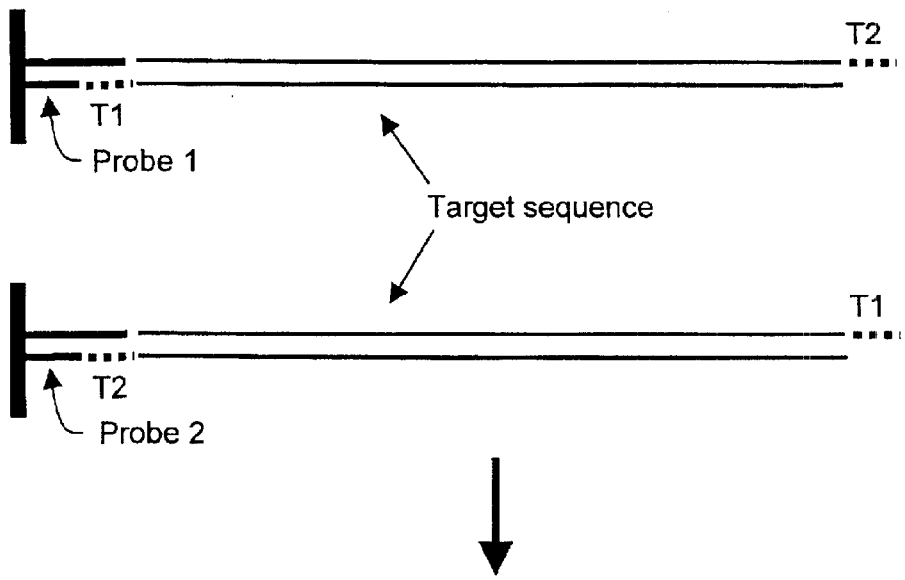
FIG. 2

5) Ligate and wash with high stringency to leave one strand of target sequence on each of the two probes 3A
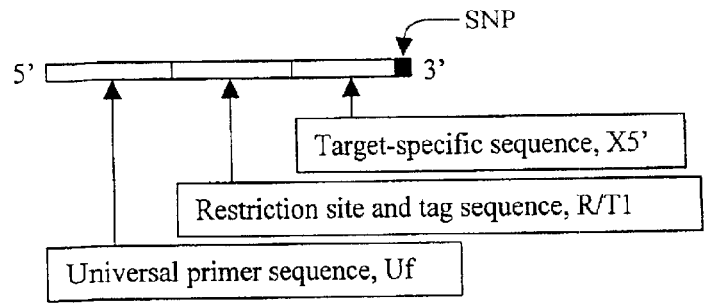
3B
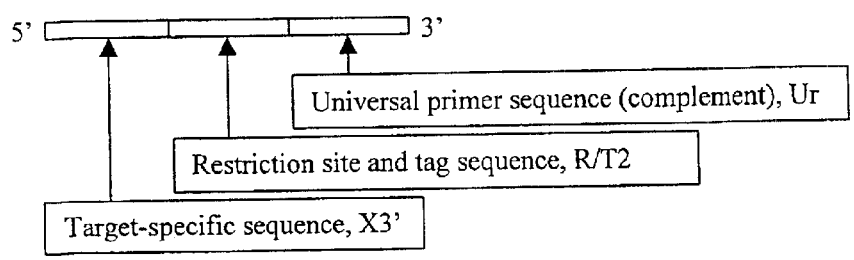
FIG. 3A-B 1) Hybridization and ligation of 5' Probe/Primer and 3' Probe/Primer to denatured (single-stranded) target sequence (1 OF 3)

2) PCR with high concentrations of universal primers, Uf and Ur
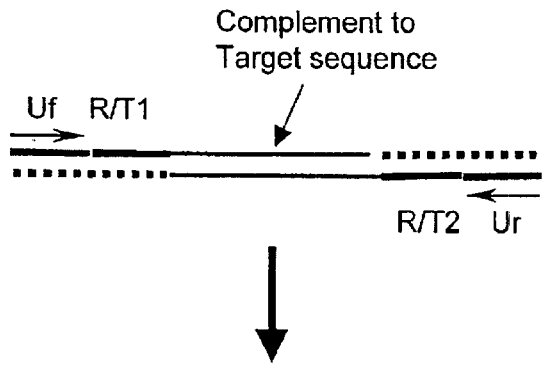
3) Digest with restriction enzyme, leaving tag sequences in the 3' overhangs at the ends of the target sequence
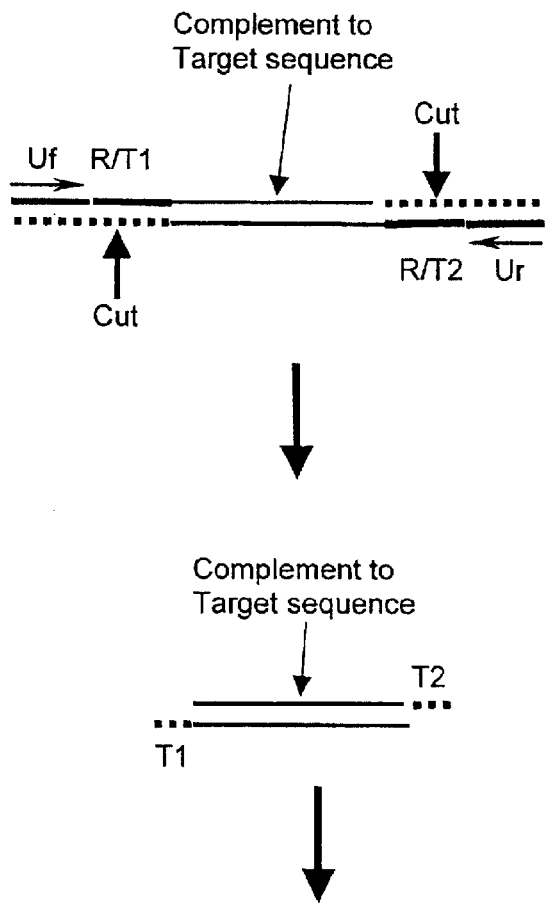
FIG. 4
(2 OF 3)

4) Capture target sequence on either or both of two partially duplex probes, complementary to tags T1 or T2.
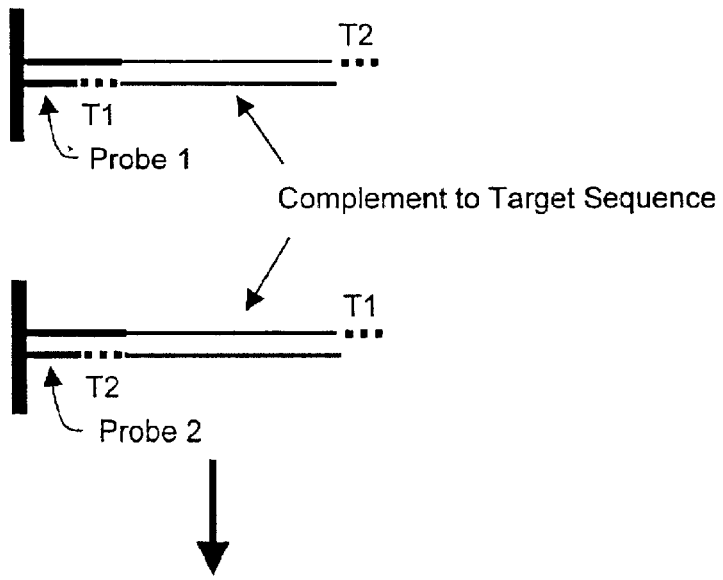
5) Ligate and wash with high stringency to leave one strand of target sequence on each of the two probes
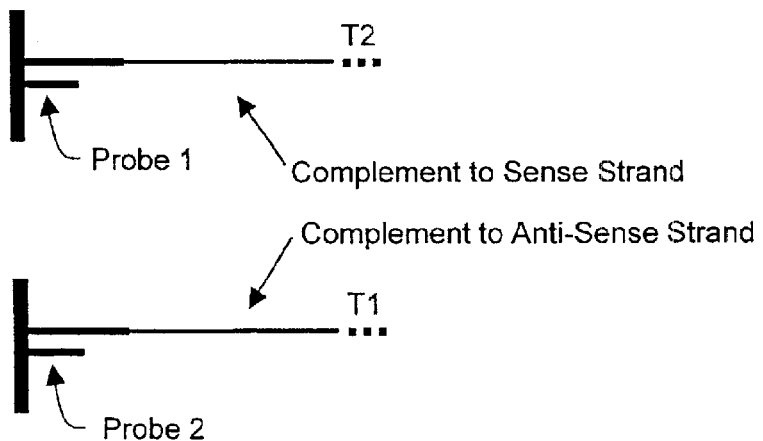
FIG. 4
(3 OF 3)

US 6,964,847 B1

DERIVATIVE NUCLEIC ACIDS AND USES THEREOF

This application claims priority from provisional patent application 60/143,804, filed Jul. 14, 1999, which is hereby incorporated by reference.

FIELD OF INVENTION

This invention relates to the field of analyzing complex mixtures of nucleic acids for the presence of specific sequences and for the presence of specific sequence variations.

BACKGROUND

Methods of the invention can be used to analyze complex mixtures of nucleic acids in small amounts of source material. Common applications are the quantification of messenger RNA levels for specific genes in an organism or tissue or the determination of the allele status of genetic polymorphisms in genomic DNA. Often there is a requirement to analyze many different nucleic acid sequences in a single sample, and it is often necessary to amplify the target nucleic acids or signal molecules to obtain detectable signals in an assay.

DNA microarrays provide the ability to analyze many target sequences in a sample. However, conventional microarray analysis is limited by the cost and difficulty of preparing large numbers of target molecules from limited amounts of sample and by poor hybridization specificity. Multiplexed analysis—amplifying target sequences or target-specific probe molecules from many targets in a single sample—can minimize the cost of reagents and the consumption of precious samples. Methods with better sequence specificity than simple hybridization reactions—e.g., analytical methods based on activities of nucleic acid modifying enzymes—provide improved reliability and accuracy of the quantification of specific sequences and the detection of specific polymorphisms.

Multiplex polymerase chain reactions (PCR) have been used to decrease the sample preparation for scoring genetic variation by hybridization on DNA microarrays. Unfortunately many of the target sequences fail to amplify optimally, especially when large multiplex factors (large numbers of target sequences amplified simultaneously) are used (Wang et al., Science 280:1077, 1998). Multiplex PCR has been performed with 5' extensions or "tails" on target-specific PCR primers which incorporate universal priming sequences into amplification products (Brownie et al, Nucleic Acids Research 25:3235, 1997; U.S. Pat. No. 5,858,989; Jeffreys et al; Favis et al, Nature Biotechnology 18:561, 2000). Amplification is performed for a limited number of cycles with these tailed target-specific primers, and then further amplification is performed with high concentrations of universal primers with the same sequence as the 5' tails of the target-specific primers.

Multiplex amplification with universal primers after appending 5' extensions on amplification products with adapter primers has been used with strand displacement amplification (U.S. Pat. No. 5,422,252, Walker et al.). Generic or universal primers have been used to amplify ligatable probes (U.S. Pat. No. 5,876,924, Zhang et al.; Thomas et al., Arch Pathol Lab Med 123:1170, 1999). The use of generic primers for probe amplification is advantageous compared to convention target amplification with PCR, since primer binding and amplification is not subject to the variability of target sequences. The ligatable probes may be pairs of linear probes or a single circularizable probe. In the case of pairs of linear probes the generic primer sequences are incorporated into the 3' and 5' ends of the probes, respectively (U.S. Pat. No. 5,876,924, Zhang et al.). In the case of circularizable probes, generic primer sequences are incorporated into the linker region between the target-specific termini of the probe. Amplification of circularizable probes may be performed with a single generic primer ("rolling circle amplification", RCA) or with a pair of generic PCR primers (U.S. Pat. No. 5,876,924, Zhang et al.; Thomas et al., Arch Pathol Lab Med 123:1170, 1999). Amplified circularizable probes are attractive alternatives to PCR for multiplexed analysis (Isaksson and Landegren, Curr Opin Biotechnol. 10:11, 1999). Ligation reaction provide excellent sequence discrimination for scoring SNPs (Thomas et al., Arch Pathol Lab Med 123:1170, 1999; Favis et al, Nature Biotechnology 18:561, 2000).

Another type of reaction that provides excellent sequence discrimination and that also provides amplification of the probes is the Invader assay developed by the Third Wave Technologies Company (U.S. Pat. No. 5,846,717; U.S. Pat. No. 5,888,780; U.S. Pat. No. 5,985,557; U.S. Pat. No. 5,994,069; U.S. Pat. No. 6,001,567). With this method pairs of probes are hybridized to nucleic acid targets, and an endonuclease enzyme effects cyclic structure-dependent cleavage of one of the probes, if the probe matches the target sequence. A fragment of arbitrary sequence with a ligatable 3' terminus ("flap") is cleaved from the probe by the enzyme. The reaction provides substantial amplification and high specificity for scoring of SNPs (Ryan et al., Mol Diagn 4:135, 1999, Griffin et al., Proc Natl Acad Sci USA 96:6301, 1999) and has great potential for multiplexing the analysis of many targets in a single sample (Griffin et al., Proc Natl Acad Sci USA 96:6301, 1999).

Capture of target sequences on microarrays of nucleic acid probes is limited by less than optimal discrimination between related but non-identical sequences and by the secondary structure of target molecules. Analysis of single nucleotide polymorphisms (SNPs) by hybridization on oligonucleotide arrays is error prone and requires the use of highly redundant sets of probes (Wang et al., Science 280:1077, 1998; Cargill et al., Nature Genetics 22: 231, 1999). A method of enhanced oligonucleotide capture uses partially duplex probes and enzymatic reactions (ligation and/or primer extension) to accurately discriminate perfectly matched targets from those containing mismatches (Broude et al., Proc. Natl. Acad. Sci. 91: 3072, 1994; U.S. Pat. No. 5,503,980, Cantor; Gunderson et al., Genome Research 8:1142, 1998). Analysis of the efficiency of hybridization of various nucleic acid sequences (Mir and Southern, Nature Biotechnology 17:788, 1999) has demonstrated that the hybridization is most efficient at single stranded regions near duplex stems, probably due to the presence of helical order and the absence of tertiary interactions. Ligation and polymerase reactions have been shown to provide excellent discrimination of perfectly and mismatched probes required for the scoring of SNPs (Thomas et al., Arch Pathol Lab Med 123:1170, 1999; Favis et al, Nature Biotechnology 18:561, 2000; Pastinen, et al., Genome Research 7:606, 1997). Thus capture of nucleic acid targets on partially duplex probes coupled with enzymatic discrimination provides for very high specificity. The probes capture only terminal sequences on target molecules; internal target sequences that match the single stranded overhang sequences of the probes are not captured.

SUMMARY OF THE INVENTION

In one aspect, the invention features, a method for multiplexed analysis of a plurality of target nucleic acid sequences in a sample. The method provides a derivative nucleic acid for each target sequence analyzed and present in the sample. A derivative nucleic acid is a nucleic acid which includes a capture tag sequence at one, or both, of its 3' and 5' termini. The derivative sequence is produced only upon the hybridization of a probe or primer which includes the sequence tag as an internal fragment to the target sequence for which it is specific. The sequence tag is analyzed, e.g., by its ability to bind to a capture probe, e.g., a capture probe bound to a insoluble substrate, e.g., a bead, or an ordered array of partially duplex capture probes. The presence of the derivative nucleic acid, and its characteristic terminal sequence tag, is diagnostic of the presence of a selected target sequence. The method can evaluate, e.g., identify or quantitate, the presence of one, or preferably a plurality, of specific nucleic acid sequences, or the presence of specific sequence variations. The method includes the steps of:

providing, for each target nucleic acid sequence to be analyzed, at least one probe/primer molecule which probe/primer molecule includes a region of sequence substantially complementary to a sequence in the target nucleic acid sequence and a region that is not located at either terminus of the probe/primer and which includes a capture tag sequence;

forming a reaction mixture which includes the probe/primer molecules and the target sequences under conditions such that, if a probe/primer molecule specific for a target sequence and that target sequence are both present, one or a plurality of derivative molecules having a capture tag at one or both its 3' or 5' termini, of the probe specific for the target sequence, is generated, thereby producing a derivative nucleic acid suitable for evaluation;

optionally, evaluating the presence of one or more sequence tags, e.g., by capturing the derivative nucleic acid molecules by hybridizing the tag sequences to complementary single stranded overhangs on partially duplex probes, which are preferably spatially separated, (e.g., on beads or on an ordered array) such that the tag sequences are contiguous with the double stranded regions of the partially duplex probes and thereby analyzing said captured derivative nucleic acid molecules. In preferred embodiments the captured derivative nucleic acids are further analyzed, e.g., SNP's or other sequence events are evaluated, e.g., by a further reaction, e.g., an extension reaction.

In a particularly preferred embodiment the derivative nucleic acid is ligated to a capture probe, e.g., to a partially duplex probe and then washed, preferably stringently washed, to achieve highly specific capture.

In a preferred embodiment a partially duplex probes include a single molecule which is partially self-complementary and forms a hairpin structure with either a 3' or 5' overhang and optionally which contains a chemical moiety that allows for the immobilization and spatial separation of the probe molecules.

In a preferred embodiment a partially duplex probes include a pair of molecules which are bound by non-covalent means to form a structure with either a 3' or 5' overhang and optionally which contains a chemical moiety on one of the molecules that allows for the immobilization and spatial separation of the probe molecules.

In a preferred embodiment the partially duplex probes consists of a pair of molecules which are bound by covalent means to form a structure with either a 3' or 5' overhang and which contains a chemical moiety on one of the molecules that allows for the immobilization and spatial separation of the probe molecules.

In another aspect, the invention features, a method of providing a derivative nucleic acid having single-strand overhang suitable for analysis. The method includes:

providing a first and second primer,
wherein said first primer includes, preferably in the order of 5' to 3',
a first region which includes a universal primer sequence (in a preferred embodiment the universal primer sequence is different for each primer of a pair, but the same pair is used for all targets) (occasionally referred to herein as Uf);
a second region which includes a capture tag sequence and a cleavage site, e.g., a site for cleavage by a restriction enzyme sequence (occasionally referred to herein as R/T), and
a third region which can which can hybridize to a first region on the target nucleic acid sequence (occasionally referred to herein as Xf), wherein said second primer includes, preferably in the order of 5' to 3',
a first region which includes a universal primer sequence (occasionally referred to herein as Ur);
a second region which includes a capture tag sequence (the capture tag sequence on the second primer can be the same or different, and is preferably of different sequence, from that of the capture tag of the first primer) and a cleavage site, e.g., a site for cleavage by a restriction enzyme sequence (occasionally referred to herein as R/T2), and
a third region which can which can hybridize to a second region on the target nucleic acid sequence (occasionally referred to herein as Xr), forming a reaction mixture which includes the first and second primers and the target nucleic acid, and using the target as a template, extending the primers along the target nucleic acid, to produce an extended target strand, which preferably includes, in order, a universal primer sequence, a capture tag sequence, target sequence, a capture tag sequence, and a universal primer sequence;

optionally amplifying, using the first and second primers, the extended target strand;

contacting an extended target strand with a universal primer which binds to the universal primer sequence (and preferably not to regions on the amplified target strand other than the universal primer sequence) and extending the universal primers along the extended target strand to synthesize a extended target strand which includes, in order, a universal primer sequence, a capture tag sequence, target sequence, a capture tag sequence, and a universal primer sequence;

optionally amplifying, using universal primers, the extended target stranded species;

cleaving at the cleavage site of one or both ends of a double stranded extended target molecule to provide a derivative nucleic acid which includes a double stranded molecule having an overhang which includes the capture tag sequence, preferably at one or both of the 3' and 5' termini, thereby producing a target molecule having an overhang.

Methods of the invention allow for multiplexed reactions, e.g., reactions in which two or more targets, and preferably as many as 10, 50, 100, 200, 500, 1000, or 5000, target sequences, are analyzed. Targets can be on the same molecule or can be on different molecules. In the examples below an embodiment wherein the targets are on different molecules is described, but the method can be used to analyze different regions of a single molecule. Thus, in a preferred embodiment the reaction mix includes a second target, and a third and a fourth probe are included in the reaction mix, wherein said third probe includes, preferably in the order of 5' to 3', a first region which includes a universal primer sequence; a second region which includes a capture tag sequence (which is preferably different form the capture tag sequence on one or both of the first and second probe) and a cleavage site, e.g., a site for cleavage by a restriction enzyme, and a third region which can hybridize to a first region on the target nucleic acid, wherein said fourth probe includes, preferably in the order of 5' to 3', a first region which can which can hybridize to a second region on the target nucleic acid (the first and second region of the target sequence can abut, or can be separated by 1 or more nucleotides, in the case where the regions about, the third and fourth probe can be joined by ligation, in the case where they are separated by one or more nucleotides the third and fourth probe/primer can be joined by polymer directed synthesis and ligation), a second region which includes a capture tag sequence (which is preferably different form the capture tag sequence one or both of the first and second primer, and which can be the same or different, and is preferably of different sequence, from that of the capture tag of the third primer) and a cleavage site, e.g., a site for cleavage by a restriction enzyme, and a third region which includes a universal primer sequence; forming a reaction mixture which includes the first, second, third and fourth probe and the two targets under condition wherein the third and fourth probe are joined, e.g., by ligation, if the second target is of a first sequence and not joined if the second target is of a second sequence, to produce a second joinde probe/ primer, which preferably includes, in order, a universal primer sequence, a capture tag sequence, target sequence, a capture tag sequence, and a universal primer sequence preferably in the order 5' to 3'; optionally, contacting a second joined probe with a pair of universal primers which bind to the universal primer sequences (and preferably not to regions on the second joined probe other than the universal primer sequences) and extending the universal primer along the second joined probe strand (or its complement) to produce one or a plurality of double strand molecules having, in order, a universal primer sequence, a capture tag sequence, second target sequence, a capture tage sequence, and a universal primer sequence; and cleaving at the cleavage site of one or both ends of a double strand joined probe to provide a derivative nucleic acid which is a double straned molecule havin overhangs which include the capture tag sequence at one or both of the 3' l and 5'termini, preferably at the 3' terminus. target sequence, a capture tag sequence, and a universal primer sequence (wherein at least one capture tag is different from a capture tag on the first extended target);

optionally amplifying, using universal primers, the extended second target strand species;

cleaving at the cleavage site of one or both ends of a double stranded second extended target molecule to provide a double stranded molecule having an overhang which include a capture tag sequence, at one or both of the 3' and 5' terminus, preferably at the 3' terminus. (Additional primers can be added to increase the number of target sequences analyzed.)

The method can further include analyzing the derivative nucleic acids of the method, e.g., by evaluating the capture tag sequence of an overhang (The derivative nucleic acids can also be analyzed by analysis of the target-specific regions of the amplicons.) The sequence of the overhang(s) can provide information as to the sequence of the target nucleic acid(s). The analysis can be performed on a duplex molecule which has an overhang at one or both ends or on single strands. One or both single strands can be analyzed. In the case where both strands are analyzed it is preferable that the sequence tags on each strand be different from one another, allowing, e.g., independent analysis, e.g., on an array of capture probes.

A preferred method of evaluating the derivative nucleic acid molecules having an overhang includes contacting the molecules with a capture probe, e.g., a capture probe bound to a insoluble substrate, e.g., a bead, or an ordered array of probes. e.g., the molecules can be hybridized to an array having a plurality of capture probes, wherein each of the capture probes is positionally distinguishable from the other capture probes of the plurality and has a unique variable region not repeated in another capture probe of the plurality. In a particularly preferred embodiment the derivative nucleic acid is ligated to a capture probe, e.g., to a partially duplex probe and then washed, preferably stringently washed, to achieve highly specific capture. The unique regions hybridize with the capture tag sequence of a single strand molecule or the single strand overhang(s) of a double stranded molecule, thereby allowing evaluation, e.g., identification or quantitation, or further analysis, e.g., sequence analysis, by a variety of analytical methods, of a target molecule. A capture probe can be single or double stranded but preferably has a double stranded region and a single stranded region preferably it has a 3' end capable of serving as a priming site for extension. Preferably the unique region is a 3' or 5' overhang preferably in the 3' single strand overhang of the capture probe. The template dependent extension of the 3' end of the capture probe is diagnostic for capture of the derivative nucleic acid. However, there are cases (e.g., when the derivative nucleic acids is to be analyzed by primer extension using a special primer) that the 3' end should be blocked so that no extension can occur.

In a preferred embodiment a partially duplex probes include a single molecule which is partially self-complementary and forms a hairpin structure with either a 3' or 5' overhang and optionally which contains a chemical moiety that allows for the immobilization and spatial separation of the probe molecules.

In a preferred embodiment a partially duplex probes include a pair of molecules which are bound by non-covalent means to form a structure with either a 3' or 5' overhang and optionally which contains a chemical moiety on one of the molecules that allows for the immobilization and spatial separation of the probe molecules.

In a preferred embodiment a partially duplex probes consists of a pair of molecules which are bound by covalent means to form a structure with either a 3' or 5' overhang and which contains a chemical moiety on one of the molecules that allows for the immobilization and spatial separation of the probe molecules.

In a preferred embodiment the array is a three-dimensional array, e.g., a gel array.

In preferred embodiments hybridization to the array is detected by any of: fluorescence, a proximity based signal generating system, or by mass spectrophotometry, e.g., by MALDI-TOF mass spectrophotometry.

In preferred embodiments the method includes one or more enzyme mediated reactions in which a nucleic acid used in the method, e.g., a capture probe or a derivative nucleic acid, is the substrate or template for the enzyme mediated reaction. This can increase the specificity of the evaluation. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme. The derivative nucleic acid sequence which hybridizes with the capture probe can be the substrate in an enzyme mediated reaction, e.g., it can be ligated to a strand of the capture probe or it can be extended along a strand of the capture probe. Alternatively, the capture probe can be extended along the derivative nucleic acid sequence. Alternatively, a separate primer can be contacted with the derivative nucleic acid for the analysis. (Any of the extension reactors discussed herein can be performed with labeled, or chain terminating, subunits.) The capture probe duplex can be the substrate for a cleavage reaction. These reactions can be used to increase specificity of the method or to otherwise aid in detection, e.g., by providing a signal. A wash following a reaction, e.g., a ligase reaction, can improve detection and/or specificity.

In a preferred embodiment the derivative nucleic acid is allowed to hybridize to the array and the 3' end of the capture probe is extend across the region of the target sequence, e.g., a genomic nucleic acid having a genetic event, with one or more terminating base species, where if more than one is used each species has a unique distinguishable label e.g. label 1 for base A, label 2 for base T, label 3 for base G, and label 4 for base C; thereby analyzing the amplified sample sequence.

In a preferred embodiment the method includes detecting a genetic event, e.g., a single nucleotide polymorphism, in a target or sample.

Methods of the invention can be used with a wide variety of samples and targets. In preferred embodiments the target is: a DNA molecule: all or part of a known gene; wild type DNA; mutant DNA; a genomic fragment, particularly a human genomic fragment; a cDNA, particularly a human cDNA. In preferred embodiments the target a cDNA the synthesis of which was directed by: an RNA molecule: an RNA transcript; wild type RNA; mutant RNA, or a human RNA. In preferred embodiments the target sequence is: a human sequence; a non-human sequence, e.g., a mouse, rat, pig, primate. In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder; to stage a disease or disorder; to determine if a party should pay for a treatment, e.g., to determine if one party, e.g., an insurance company or government, should pay or reimburse a party which has paid for a treatment.

Methods of U.S. Pat. No. 5,503,980 and or U.S. Pat. No. 5,631,134, both of which are hereby incorporated by reference can be used herein, particularly, the array and array-related steps recited herein can use methods taught in these patents.

In another aspect, the invention features, a method of using ligatable probes to provide a nucleic acid having single-strand overhangs suitable for analysis preferably a double strand nucleic acid with single strand overhangs at one or both ends, suitable for multiplex analysis e.g., suitable e.g., for detecting one or more genetic events, e.g., one or more single nucleotide polymorphisms, in a sample.

The method includes:

providing a first and second probe,
  wherein said first probe includes, preferably in the order of 5' to 3',
    a first region which includes a universal primer sequence (referred to occasionally herein as Uf);
    a second region which includes a capture tag sequence and a cleavage site, e.g., a site for cleavage by a restriction enzyme (referred to occasionally herein as R/T1), and
    a third region which can which can hybridize to a first region on the target nucleic acid (referred to occasionally herein as X5'), wherein said second probe/primer includes, preferably in the order of 3' to
    a first region which can which can hybridize to a second region on the target nucleic acid (the first and second region of the target sequence can abut, or can be separated e.g., by 1 or up to 2, 3, 4, 5, 10 or 20 nucleotides, in the case where the regions, the first and second probe can be joined by ligation, in the case where they are separated by one or more nucleotides the first and second primer can be joined by polymerase directed synthesis and ligation) (referred to occasionally herein as X3'),
    a second region which includes a capture tag sequence (the capture tag sequence on the second probe can be the same or different, and is preferably of different sequence, from that of the capture tag of the first probe) and a cleavage site, e.g., a site for cleavage by a restriction enzyme (referred to occasionally herein as R/T2), and
    a third region which includes a universal primer sequence (referred to occasionally herein as Ur);

forming a reaction mixture which includes the first and second probes and the target nucleic, under conditions wherein the first and second probes are joined, e.g., by ligation, if the target is of a first sequence and not joined if the target is of a second sequence, to produce a joined probe, which preferably includes, in order, a universal primer sequence, a capture tag sequence, target sequence, a capture tag sequence, and a universal primer sequence, preferably in the order 5' to 3';

optionally, contacting a joined probe with a pair of universal primers which bind to the universal primer sequences (and preferably not to regions on the joined probe other than the universal primer sequences) and extending the universal primer sequences along the joined probe strand (or its complement) to produce one or a plurality of double stranded molecules having, in order, a universal primer sequence, a capture tag sequence, target sequence, a capture tag sequence, and a universal primer sequence;

cleaving at the cleavage site of one or both ends of a double stranded extended target molecule to provide a derivative nucleic acid which is a double stranded molecule having overhangs which include the capture tag sequence at one or both of the 3' and 5' termini, preferably at the 3' terminus.

thereby producing a target molecule having overhangs.

Methods of the invention allow for multiplexed reactions, e.g., reactions in which two or more targets, and preferably as many as 10, 50, 100, 200, 500, 1000, or 5000 target sequences, are analyzed. Targets can be on the same molecule or can be on different molecules. In the examples below an embodiment wherein the targets are on different molecules is described, but the method can be used to analyze different regions of a single molecule. Thus, in a preferred embodiment the reaction mix includes a second target, and a third and a forth probe are included in the reaction mix, wherein said third probe includes, preferably in the order of 5' to 3',
  a first region which includes a universal primer sequence;
  a second region which includes a capture tag sequence (which is preferably different form the capture tag sequence on one or both of the first and second probe) and a cleavage site, e.g., a site for cleavage by a restriction enzyme, and
  a third region which can which can hybridize to a first region on the target nucleic acid, wherein said fourth probe includes, preferably in the order of 5' to 3',
  a first region which can which can hybridize to a second region on the target nucleic acid (the first and second region of the target sequence can abut, or can be separated by 1 or nucleotides, in the case where the regions about, the third and fourth probe can be joined by ligation, in the case where they are separated by one or more nucleotides the third and fourth probe/primer can be joined by polymerase directed synthesis and ligation),
  a second region which includes a capture tag sequence (which is preferably different form the capture tag sequence on one or both of the first and second primer, and which can be the same or different, and is preferably of different sequence, from that of the capture tag of the third primer) and a cleavage site, e.g., a site for cleavage by a restriction enzyme, and
  a third region which includes a universal primer sequence;

forming a reaction mixture which includes the first, second, third and fourth probe and the two targets under conditions wherein the third and fourth probe are joined, e.g., by ligation, if the second target is of a first sequence and not joined if the second target is of a second sequence, to produce a second joined probe/ primer, which preferably includes, in order, a universal primer sequence, a capture tag sequence, target sequence, a capture tag sequence, and a universal primer sequence, preferably in the order 5' to 3';

optionally, contacting a second joined probe with a pair of universal primers which bind to the universal primer sequences (and preferably not to regions on the second joined probe other than the universal primer sequences) and extending the universal primers along the second joined probe strand (or its complement) to produce one or a plurality of double stranded molecules having, in order, a universal primer sequence, a capture tag sequence, second target sequence, a capture tag sequence, and a universal primer sequence;

cleaving at the cleavage site of one or both ends of a double strand joined probe to provide a derivative nucleic acid which is a double stranded molecule having overhangs which include the capture tag sequence at one or both of the 3' and 5' termini, preferably at the 3' terminus, The method can further include analyzing the derivative nucleic acids of the method, e.g., by evaluating the capture tag sequence of an overhang (The derivative nucleic acids can also be analyzed by analysis of the target-specific regions of the amplicons). The sequence of the overhang(s) can provide information as to the sequence of the target nucleic acid(s). The analysis can be performed on a duplex molecule which has an overhang at one or both ends or on single strands. One or both single strands can be analyzed. In the case where both strands are analyzed it is preferable that the sequence tags on each strand be different from one another, allowing, e.g., independent analysis, e.g., on an array of capture probes.

A preferred method of evaluating the derivative nucleic acid molecules having an overhang includes contacting the molecules with a capture probe, e.g., a capture probe bound to a insoluble substrate, e.g., a bead, or an ordered array of probes. E.g., the molecules can be hybridized to an array having a plurality of capture probes, wherein each of the capture probes is positionally distinguishable from the other capture probes of the plurality and has a unique variable region not repeated in another capture probe of the plurality. In a particularly preferred embodiment the derivative nucleic acid is ligated to a capture probe, e.g., to a partially duplex probe and then washed, preferably stringently washed, to achieve highly specific capture. The unique regions hybridize with the capture tag sequence of a single strand molecule or the single strand overhang(s) of a double stranded molecule, thereby allowing evaluation, e.g., identification or quantitation, or further analysis, e.g., sequence analysis, by a variety of analytical methods, of a target molecule. A capture probe can be single or double stranded but preferably has a double stranded region and a single stranded region. Preferably it has a 3' end capable of serving as a priming site for extension. Preferably the unique region is in a 3' or 5' overhang preferably the 3' single strand overhang of the capture probe. The template dependent extension of the 3' end of the capture probe is diagnostic for capture of the derivative nucleic acid. However, there are cases (e.g., when the derivative nucleic acids is to be analyzed by primer extension using a special primer) that the 3' end should be blocked so that no extension can occur.

In a preferred embodiment a partially duplex probes include a single molecule which is partially self-complementary and forms a hairpin structure with either a 3' or 5' overhang and optionally which contains a chemical moiety that allows for the immobilization and spatial separation of the probe molecules.

In a preferred embodiment a partially duplex probes include a pair of molecules which are bound by non-covalent means to form a structure with either a 3' or 5' overhang and optionally which contains a chemical moiety on one of the molecules that allows for the immobilization and spatial separation of the probe molecules.

In a preferred embodiment a partially duplex probes consists of a pair of molecules which are bound by covalent means to form a structure with either a 3' or 5' overhang and which contains a chemical moiety on one of the molecules that allows for the immobilization and spatial separation of the probe molecules.

In a preferred embodiment the array is a three-dimensional array, e.g., a gel array.

In preferred embodiments hybridization to the array is detected by any of: fluorescence, a proximity based signal generating system, or by mass spectrophotometry, e.g., by MALDI-TOF mass spectrophotometry.

In preferred embodiments the method includes one or more enzyme mediated reactions in which a nucleic acid used in the method, e.g., a capture probe or a derivative nucleic acid, is the substrate or template for the enzyme mediated reaction. This can increase the specificity of the evaluation. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme. The derivative nucleic acid sequence which hybridizes with the capture probe can be the substrate in an enzyme mediated reaction, e.g., it can be ligated to a strand of the capture probe or it can be extended along a strand of the capture probe. Alternatively, the capture probe can be extended along the derivative nucleic acid sequence. Alternatively, a separate primer can be contacted with the derivative nucleic acid for the analysis. (Any of the extension reactors discussed herein can be performed with labeled, or chain terminating, subunits.) The capture probe duplex can be the substrate for a cleavage reaction. These reactions can be used to increase specificity of the method or to otherwise aid in detection, e.g., by providing a signal. A wash following a reaction, e.g., a ligase reaction, can improve detection and/or specificity.

In a preferred embodiment the method includes detecting a genetic event, e.g., a single nucleotide polymorphism, in a target or sample.

Methods of the invention can be used with a wide variety of samples and targets. In preferred embodiments the target is: a DNA molecule: all or part of a known gene; wild type DNA; mutant DNA; a genomic fragment, particularly a human genomic fragment; a cDNA, particularly a human cDNA. In preferred embodiments the target a cDNA the synthesis of which was directed by: an RNA molecule: an RNA transcript; wild type RNA; mutant RNA, or a human RNA. In preferred embodiments the target sequence is: a human sequence; a non-human sequence, e.g., a mouse, rat, pig, primate. In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder; to stage a disease or disorder, to determine if a party should pay for a treatment, e.g., to determine if one party, e.g., an insurance company or government, should pay or reimburse a party which has paid for a treatment.

In one aspect, the invention features a method of providing a nucleic acid with single strand overhang, preferably a double strand nucleic acid with single strand overhangs at one or both ends, suitable for multiplex analysis, e.g., suitable for detecting one or more genetic events, e.g., one or more single nucleotide polymorphisms, in a sample.

The method includes:

(1) providing a sample which includes one or a plurality of target nucleic acid sequences;

(2) providing a first single stranded linear probe, wherein the first single-stranded linear probe includes, at one terminus, a first region which is complementary to a first region on a first target, and at its other terminus a second region which is complementary to a second region on a first target, wherein the first and second region on the first target can be directly or can be separated by one or more nucleotides (upon hybridization of the first and second regions to the target, the termini of the probe can be joined, e.g., by ligation, or by polymerase catalyzed extension and ligation, thus the probe will be circularized only when the target sequence for which the probe is specific is present in the sample), a cleavage site a capture tag sequence, wherein the cleavage site and capture tag sequence are disposed such that cleavage results in a single-stranded overhang, at one or both of the 3' and 5' termini, preferably a 3' single stranded overhang, which includes at its terminus, the capture sequence tag, and a universal primer sequence;

(3) providing a second single stranded linear probe, wherein the second single-stranded probe includes, at one terminus, a first region which is complementary to a first region on a second target, and at its other terminus a second region which is complementary to a second region on a second target, wherein the first and second region on the first target can be directly or can be separated by one or more nucleotides, a cleavage site a capture tag sequence, which capture sequence preferably differs in sequence from the capture tag on the first single stranded probe, and wherein the cleavage site and capture tag sequence are disposed such that cleavage results in a single-stranded overhang, at one or both of its 3' and 5' termini, preferably a 3' single stranded overhang, which includes at its terminus, the capture sequence tag, and a universal primer sequence, which is preferably, of the same sequence as the universal primer sequence on the first single stranded probe;

contacting the first single stranded probe with the first target and the second single stranded probe with the second target under conditions which allow the circularization of the a single stranded circular probe if to be circularized if a target is present which is homologous to its terminal target binding regions;

contacting the first and second probes with a universal primer under conditions which allow rolling circle amplification and produce double stranded amplification product;

cleaving the double stranded amplification product at cleavage sites, e.g., with a restriction enzyme, e.g., a type II restriction enzyme, to provide cleaved product having a capture tag sequence at the terminus of a single stranded overhang.

The method can further include analyzing the derivative nucleic acids of the method, e.g., by evaluating the capture tag sequence of an overhang (The derivative nucleic acids can also be analyzed by analysis of the target-specific regions of the amplicons). The sequence of the overhang(s) can provide information as to the sequence of the target nucleic acid(s). The analysis can be performed on a duplex molecule which has an overhang at one or both ends or on single strands. One or both single strands can be analyzed. In the case where both strands are analyzed it is preferable that the sequence tags on each strand be different from one another, allowing, e.g., independent analysis, e.g., on an array of capture probes.

A preferred method of evaluating the derivative nucleic acid molecules having an overhang includes contacting the molecules with a capture probe, e.g., a capture probe bound to a insoluble substrate, e.g., a bead, or an ordered array of probes. E.g., the molecules can be hybridized to an array having a plurality of capture probes, wherein each of the capture probes is positionally distinguishable from the other capture probes of the plurality and has a unique variable region not repeated in another capture probe of the plurality.

In a particularly preferred embodiment the derivative nucleic acid is ligated to a capture probe, e.g., to a partially duplex probe and then washed, preferably stringently washed, to achieve highly specific capture. The unique regions hybridize with the capture tag sequence of a single strand molecule or the single strand overhang(s) of a double stranded molecule, thereby allowing evaluation, e.g., identification or quantitation, or further analysis, e.g., sequence analysis, by a variety of analytical methods, of a target molecule. A capture probe can be single or double stranded but preferably has a double stranded region and a single stranded region. Preferably it has a 3' end capable of serving as a priming site for extension. Preferably the unique region is in a 3' or 5' overhang, preferably the 3' single strand overhang of the capture probe. The template dependent extension of the 3' end of the capture probe is diagnostic for capture of the derivative nucleic acid. However, there are cases (e.g., when the derivative nucleic acids is to be analyzed by primer extension using a special primer) that the 3' end should be blocked so that no extension can occur.

In a preferred embodiment the partially duplex probes include a single molecule which is partially self-complementary and forms a hairpin structure with either a 3' or 5' overhang and optionally which contains a chemical moiety that allows for the immobilization and spatial separation of the probe molecules.

In a preferred embodiment the partially duplex probes include a pair of molecules which are bound by non-covalent means to form a structure with either a 3' or 5' overhang and optionally which contains a chemical moiety on one of the molecules that allows for the immobilization and spatial separation of the probe molecules.

In a preferred embodiment the partially duplex probes consists of a pair of molecules which are bound by covalent means to form a structure with either a 3' or 5' overhang and which contains a chemical moiety on one of the molecules that allows for the immobilization and spatial separation of the probe molecules.

In a preferred embodiment the array is a three-dimensional array, e.g., a gel array.

In preferred embodiments hybridization to the array is detected by any of: fluorescence, a proximity based signal generating system, or by mass spectrophotometry, e.g., by MALDI-TOF mass spectrophotometry.

In preferred embodiments the method includes one or more enzyme mediated reactions in which a nucleic acid used in the method, e.g., a capture probe or a derivative nucleic acid, is the substrate or template for the enzyme mediated reaction. This can increase the specificity of the evaluation. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme. The derivative nucleic acid sequence which hybridizes with the capture probe can be the substrate in an enzyme mediated reaction, e.g., it can be ligated to a strand of the capture probe or it can be extended along a strand of the capture probe. Alternatively, the capture probe can be extended along the derivative nucleic acid sequence. Alternatively, a separate primer can be contacted with the derivative nucleic acid for the analysis. (Any of the extension reactors discussed herein can be performed with labeled, or chain terminating, subunits.) The capture probe duplex can be the substrate for a cleavage reaction. These reactions can be used to increase specificity of the method or to otherwise aid in detection, e.g., by providing a signal. A wash following a reaction, e.g., a ligase reaction, can improve detection and/or specificity.

In a preferred embodiment the derivative nucleic acid is allowed to hybridize to the array and the 3' end of the capture probe is extend across the region of the target sequence, e.g., a genomic nucleic acid having a genetic event, with one or more terminating base species, where if more than one is used each species has a unique distinguishable label e.g. label 1 for base A, label 2 for base T, label 3 for base G, and label 4 for base C; thereby analyzing the amplified sample sequence.

In a preferred embodiment the method includes detecting a genetic event, e.g., a single nucleotide polymorphism, in a target or sample.

In preferred embodiments, a genetic event is within a region which hybridizes to a probe, e.g., is 1, 2, 3, 4 or 5 base pairs from the end of a region which hybridizes to a probe, or is at or sufficiently close to the end of the a region which hybridizes to a probe that a mismatch would inhibit ligation or DNA polymerase-based extension.

Methods of the invention can be used with a wide variety of samples and targets. In preferred embodiments the target is: a DNA molecule: all or part of a known gene; wild type DNA; mutant DNA; a genomic fragment, particularly a human genomic fragment; a cDNA, particularly a human cDNA. In preferred embodiments the target a cDNA the synthesis of which was directed by: an RNA molecule: an RNA transcript; wild type RNA; mutant RNA, or a human RNA. In preferred embodiments the target sequence is: a human sequence; a non-human sequence, e.g., a mouse, rat, pig, primate. In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder, to stage a disease or disorder; to determine if a party should pay for a treatment, e.g., to determine if one party, e.g., an insurance company or government, should pay or reimburse a party which has paid for a treatment.

In a preferred embodiment the single stranded linearized circular probe will have its termini joined only when there is perfect complementarity between the regions of the probe which hybridize to the target and the target.

In a preferred embodiment more than two, e.g., and as many as 10, 50, 100, 200, 500, 1000, or 5000 target sequences are present and a single strand linearized circular probe specific for each is contacted with the sample.

In some embodiments a single nucleic acid molecule will include more than one target sequence, in others, target sequences are on separate molecules, e.g., separate restriction or shear fragments.

In a preferred embodiment the method is used to detect a genetic event, e.g., a mutation or an SNP, in a target sequence. The nucleotide at complementary to the genetic event or to a nucleotide of a genetic event, can be degenerate, e.g., the method can include the use of a plurality of primers which differ from each other at the interrogation site, e.g., four primers, one each with a, g, c, and t, at the interrogation site. Each of the plurality of primers will have a different capture tag, thus the method allows identification or sequencing of the nucleotide of interest.

(b) combining the circular template with an effective amount of a RCA primer, at least two types of nucleotide triphosphates and an effective amount of a polymerase enzyme to yield a product, e.g., a single-stranded oligonucleotide multimer complementary to the circular oligonucleotide template; and In preferred embodiments amplification reactions are performed isothermally.

In preferred embodiments, analyzing a sample polynucleotide sequence includes, e.g., sequencing the polynucleotide sequence, e.g., by sequencing by hybridization or positional sequencing by hybridization, detecting the presence of, or identifying, a genetic event, e.g., a SNP, in a target nucleic acid, e.g., a DNA.

In preferred embodiments, the genetic event is within 1, 2, 3, 4 or 5 base pairs from the end of the target region which hybridizes to the probe, or is sufficiently close to the end of the target region which hybridizes to the probe that a mismatch would inhibit DNA polymerase-based extension from a target/ primed circle.

In preferred embodiments, the target nucleic acid is amplified, e.g., by PCR, prior to contact with a circular template.

Preferably, a circular template has about 15–1500 nucleotides, and more preferably about 24–500 nucleotides and most preferably about 30–150 nucleotides.

The polymerase enzyme can be any that effects the synthesis of the multimer, e.g., any polymerase described in U.S. Pat. No. 5,714,320. Generally, the definitions provided for circular vectors and their amplification in U.S. Pat. No. 5,714,320, apply to terms used herein, unless there is a conflict between the terms in which case the meaning provided herein controls. U.S. Pat. No. 5,714,320, and all other U.S. patents mentioned herein are incorporated by reference.

In another aspect, the invention features a method of providing a nucleic acid with single strand overhang, preferably a double strand nucleic acid with single strand overhangs at one or both ends, suitable for multiplex analysis e.g., suitable for detecting one or more genetic events, e.g., one or more single nucleotide polymorphisms, in a sample.

The method includes:

(a) providing a target nucleic acid having a first and second region, wherein the two regions preferably overlap;

providing an invader probe which is complementary to the first region of the target, providing a signal probe having, in the 5' to 3' direction, (optionally) a signal sequence, a capture tag sequence, and a region complementary to the second region of the target nucleic acid;

(b) contacting the target sequence with the invader probe and the signal probe, under conditions wherein the invader probe and an end, e.g., the 3' end of the signal probe are annealed to the target nucleic acid sequence so as to create a cleavage structure having a single-stranded arm which includes, optionally, the signal sequence, and the capture tag;

(c) cleaving the first cleavage structure under conditions such that cleavage of the cleavage structure occurs at a site located within the signal probe in a manner dependent upon the annealing of the invader and signal probes on the target nucleic acid such that cleavage liberates the single-stranded arm of the cleavage structure to generate a derivative nucleic acid which has the capture tag sequence at a terminus, preferably its 3' terminus;

(d) optionally allowing a subsequent, or a plurality of subsequent copies of the signal probe to anneal and be cleaved to produce an additional or a plurality of additional derivative nucleic acids which have the capture tag sequence at a terminus, preferably the 3' terminus;

thereby providing a derivative nucleic acid suitable for analysis.

In a preferred embodiment, the signal probe can include a sequence 5' to the capture tag which self hybridizes to form a hairpin structure, such that cleavage results in a structure having a hair pin with a single strand overhang. The capture tag is on the single strand overhangs which is preferably a 3' overhang.

Methods of the invention allow for multiplexed reactions, e.g., reactions in which two or more targets, and preferably as many as 10, 50, 100, 200, 500, 1000, or 5000, are analyzed. Targets can be on the same molecule or can be on different molecules. In the examples below an embodiment wherein the targets are on different molecules is described, but the method can be used to analyze different regions of a single molecule. Thus, in a preferred embodiment the reaction mix includes a second target having a first and second region, and a second invader and signal probe, wherein the second invader probe is complementary to a first region of a second target, the second signal probe includes, in the 5' to 3' direction, (optionally) a signal sequence, a capture tag sequence (which is preferably different in sequence from the capture tag sequence on the first signal probe, and a region complementary to a second region of the second target nucleic acid;

(b) contacting the second target sequence with the second invader probe and the second signal probe, under conditions wherein the second invader probe and an end, e.g., the 3' end of the second signal probe are annealed to the second target nucleic acid sequence so as to create a second cleavage structure having a single-stranded arm which includes, optionally, the signal sequences, and the capture tag;

(c) cleaving the second cleavage structure under conditions such that cleavage of the second cleavage structure occurs at a site located within the second signal probe in a manner dependent upon the annealing of the second invader and signal probes on the target nucleic acid such that cleavage liberates the single-stranded arm of the cleavage structure to generate a second derivative nucleic acid which has the capture tag sequence at a terminus, preferably its 3' terminus;

(d) optionally allowing a subsequent, or a plurality of subsequent copies of the second signal probe to anneal and be cleaved to produce an additional or a plurality of additional derivative nucleic acids which have the capture tag sequence at a terminus, preferably the 3' terminus.

In a preferred embodiment, the signal probe can include a sequence 5' to the capture tag which self hybridizes to form a hairpin structure, such that cleavage results in a structure having a hair pin with a single strand overhang. The capture tag is on the single strand overhangs which is preferably a 3' overhang.

The method can further include analyzing the derivative nucleic acids of the method, e.g., by evaluating the capture tag sequence of an overhang (The derivative nucleic acids can also be analyzed by analysis of the target-specific regions of the amplicons). The sequence of the overhang(s) can provide information as to the sequence of the target nucleic acid(s). The analysis can be performed on a duplex molecule which has an overhang at one or both ends or on single strands. One or both single strands can be analyzed. In the case where both strands are analyzed it is preferable that the sequence tags on each strand be different from one another, allowing, e.g., independent analysis, e.g., on an array of capture probes.

A preferred method of evaluating the derivative nucleic acid molecules having an overhang includes contacting the molecules with a capture probe, e.g., a capture probe bound to a insoluble substrate, e.g., a bead, or an ordered array of probes. E.g., the molecules can be hybridized to an array having a plurality of capture probes, wherein each of the capture probes is positionally distinguishable from the other capture probes of the plurality and has a unique variable region not repeated in another capture probe of the plurality. In a particularly preferred embodiment the derivative nucleic acid is ligated to a capture probe, e.g., to a partially duplex probe and then washed, preferably stringently washed, to achieve highly specific capture. The unique regions hybridize with the capture tag sequence of a single strand molecule or the single strand overhang(s) of a double stranded molecule, thereby allowing evaluation, e.g., identification or quantitation, or further analysis, e.g., sequence analysis, by a variety of analytical methods, of a target molecule. A capture probe can be single or double stranded but preferably has a double stranded region and a single stranded region. Preferably it has a 3' end capable of serving as a priming site for extension. Preferably the unique region is in a 3' or 5' overhang, preferably the 3' single strand overhang of the capture probe. The template dependent extension of the 3' end of the capture probe can be diagnostic for capture of the derivative nucleic acid. However, there are cases (e.g., when the derivative nucleic acids is to be analyzed by primer extension using a special primer) that the 3' end should be blocked so that no extension can occur.

In a preferred embodiment a partially duplex probes include a single molecule which is partially self-complementary and forms a hairpin structure with either a 3' or 5' overhang and optionally which contains a chemical moiety that allows for the immobilization and spatial separation of the probe molecules.

In a preferred embodiment a partially duplex probes include a pair of molecules which are bound by non-covalent means to form a structure with either a 3' or 5' overhang and optionally which contains a chemical moiety on one of the molecules that allows for the immobilization and spatial separation of the probe molecules.

In a preferred embodiment a partially duplex probes consists of a pair of molecules which are bound by covalent means to form a structure with either a 3' or 5' overhang and which contains a chemical moiety on one of the molecules that allows for the immobilization and spatial separation of the probe molecules.

In a preferred embodiment the array is a three-dimensional array, e.g., a gel array.

In preferred embodiments hybridization to the array is detected by any of: fluorescence, a proximity based signal generating system, or by mass spectrophotometry, e.g., by MALDI-TOF mass spectrophotometry.

In preferred embodiments the method includes one or more enzyme mediated reactions in which a nucleic acid used in the method, e.g., a capture probe or a derivative nucleic acid, is the substrate or template for the enzyme mediated reaction. This can increase the specificity of the evaluation. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIs enzyme. The derivative nucleic acid sequence which hybridizes with the capture probe can be the substrate in an enzyme mediated reaction, e.g., it can be ligated to a strand of the capture probe or it can be extended along a strand of the capture probe. Alternatively, the capture probe can be extended along the derivative nucleic acid sequence. Alternatively, a separate primer can be contacted with the derivative nucleic acid for the analysis. (Any of the extension reactors discussed herein can be performed with labeled, or chain terminating, subunits.) The capture probe duplex can be the substrate for a cleavage reaction. These reactions can be used to increase specificity of the method or to otherwise aid in detection, e.g., by providing a signal. A wash following a reaction, e.g., a ligase reaction, can improve detection and/or specificity.

In a preferred embodiment the derivative nucleic acid is allowed to hybridize to the array and the 3' end of the capture probe is extend across the region of the target sequence, e.g., a genomic nucleic acid having a genetic event, with one or more terminating base species, where if more than one is used each species has a unique distinguishable label e.g. label 1 for base A, label 2 for base T, label 3 for base G, and label 4 for base C; thereby analyzing the amplified sample sequence.

In a preferred embodiment the method includes detecting a genetic event, e.g., a single nucleotide polymorphism, in a target or sample.

In preferred embodiments, a genetic event is within a region which hybridizes to a probe, e.g., is 1, 2, 3, 4 or 5 base pairs from the end of a region which hybridizes to a probe, or is at or sufficiently close to the end of the a region which hybridizes to a probe that a mismatch would inhibit ligation or DNA polymerase-based extension.

Methods of the invention can be used with a wide variety of samples and targets. In preferred embodiments the target is: a DNA molecule: all or part of a known gene; wild type DNA; mutant DNA; a genomic fragment, particularly a human genomic fragment; a cDNA, particularly a human cDNA. In preferred embodiments the target a cDNA the synthesis of which was directed by: an RNA molecule: an RNA transcript; wild type RNA; mutant RNA, or a human RNA. In preferred embodiments the target sequence is: a human sequence; a non-human sequence, e.g., a mouse, rat, pig, primate. In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder; to stage a disease or disorder; to determine if a party should pay for a treatment, e.g., to determine if one party, e.g., an insurance company or government, should pay or reimburse a party which has paid for a treatment.

The cleavage structure can be cleaved with, e.g., a cleavage agent, such as those described in U.S. Pat. No. 5,871, 911. By "cleavage agent" is meant a molecule such as a DNA polymerase (DNAP), a domain of a DNAP, or a synthetically created protein or peptide, capable of cleaving a cleavage structure at a specific site. These enzymes are sometimes referred to as "cleavases" or as "flap endonucleases". This activity is sometimes associated with polymerases, but the activity of course is always an endonuclease. A preferable example of a cleavage agent is a 5' nuclease activity of DNAP, such as DNAPTaq, DNAPTfl, DNAPTth and DNAPEcl. After exposing the cleavage structure to a cleavage agent, the structure and agent are incubated under conditions wherein cleavage can occur.

The derivative nucleic acid has a capture tag sequence, e.g., a sequence which is complementary to capture array probes. The sequences complementary to capture probes can be positioned within the second oligonucleotide such that they are at the 3' end of the third oligonucleotide upon cleavage of the second oligonucleotide. Thus, products from a multiplexed assay can be captured at different positions on an array of capture probes.

In some embodiments, the sequence at the 5' end of the derivative nucleic acid includes an arbitrary sequence and can includes a label, e.g., a primary label, such as biotin. When biotin us used, a streptavidin labeled enzyme can be attached to detect the captured third oligonucleotide.

In some embodiments, the 5' end of the derivative nucleic acid includes a sequence tag, which can encode information, e.g., a specific allele for a polymorphic DNA sequence. The information can be detected using different reporter moieties, e.g., different colors of fluorophors. In some embodiments, the third oligonucleotide is detected using enzyme-based chemiluminescence or fluorogenic amplification.

In some embodiments, the method is used to analyze a genetic even, e.g., a SNP or a mutation. The genetic event can occur in the first region, the second region, or at the junction of the two regions.

In some embodiments, a biallelic or multi-allelic SNP is analyzed.

In some embodiments, the third oligonucleotides from a plurality of sites are analyzed.

In some embodiments, the derivative nucleic acid is further amplified, e.g., by an isothermal method, prior to further analysis, e.g., prior to hybridization to the capture probe array. The amplification can include, e.g., rolling circle amplification (RCA). When RCA is used, the method can include:

(a) annealing an effective amount of the derivative nucleic acid to a single-stranded circular template to yield an annealed circular template, wherein the single-stranded circular template comprises (i) at least one copy of a nucleotide sequence complementary to the sequence of the derivative nucleic acid and optionally, (ii) at least one nucleotide effective to produce a cleavage site in an oligonucleotide multimer;

(b) providing the primed circular template with effective amounts of a primer, at least two types of nucleotide triphosphates and a polymerase enzyme, to yield a single-stranded oligonucleotide multimer complementary to the circular oligonucleotide template, wherein the oligonucleotide multimer comprises multiple copies (amplified) of the sample sequence; optionally, (c) cleaving the oligonucleotide multimer at the cleavage site to produce the cleaved amplified sample nucleic acid; and (d) hybridizing the cleaved sample nucleic acid to the array of capture probes.

In some embodiments, the method is used to detect single nucleotide polymorphisms (SNPs). Two different probes can be encoded with different tag sequences. Multiple pairs of signal probes can be used simultaneously with the same sample to multiplex the analysis of many target sequences. The products of the reaction can then be analyzed on a capture probe array, e.g., a PSBH array.

Methods of the invention allow for the capture of cleavage products from cleavase invader assays. Accordingly, in one aspect, the invention includes a method of analyzing a polynucleotide sequence, e.g., a specific target nucleic acid molecule. The method includes:

(a) providing (i) a target nucleic acid having a first and second portion; (ii) a first oligonucleotide complementary to the first portion of the target nucleic acid; and (ii) a second oligonucleotide having a 5' and 3' end and a region complementary to the second portion of the target nucleic acid, as well as a region which is not complementary to the target nucleic acid;

(b) mixing the target nucleic acid, first oligonucleotide, and second nucleotide under conditions in which the first oligonucleotide and an end, e.g., the 3' end of the second oligonucleotide are annealed to the target nucleic acid sequence so as to create a cleavage structure having a single-stranded arm;

(c) cleaving the first cleavage structure under conditions such that cleavage of the cleavage structure occurs at a site located within the second oligonucleotide in a manner dependent upon the annealing of the first and second oligonucleotides on the target nucleic acid such that cleavage liberates the single-stranded arm of the cleavage structure to generate a third oligonucleotide;

(d) providing an array of a plurality of capture probes, wherein each of the capture probes is positionally distinguishable from other capture probes of the plurality on the array and wherein each of the capture probes contains a region of unique sequence; and (e) hybridizing the third oligonucleotide with the array of capture probes, thereby analyzing the sample sequence.

The cleavage structure can be cleaved with, e.g., a cleavage agent, such as those described in U.S. Pat. No. 5,871, 911. By "cleavage agent" is meant a molecule such as a DNA polymerase (DNAP), a domain of a DNAP, or a synthetically created protein or peptide, capable of cleaving a cleavage structure at a specific site. A preferable example of a cleavage agent is a 5' nuclease activity of DNAP, such as DNAPTaq, DNAPTfl, DNAPTth and DNAPEcl. After exposing the cleavage structure to a cleavage agent, the structure and agent are incubated under conditions wherein cleavage can occur.

In some embodiments, the third oligonucleotide has an arbitrary sequence, e.g., a sequence which includes an arbitrary tag sequence complementary to capture array probes. The sequences complementary to capture probes can be positioned within the second oligonucleotide such that they are at the 3' end of the third oligonucleotide upon cleavage of the second oligonucleotide. Thus, products from a multiplexed assay can be captured at different positions on an array of capture probes.

In some embodiments, the sequence at the 5' end of the third oligonucleotide includes an arbitrary sequence and includes a label, e.g., a primary label, such as biotin. When biotin us used, a streptavidin labeled enzyme can be attached to detect the captured third oligonucleotide.

In some embodiments, the 5' end of the third oligonucleotide includes a sequence tag, which can encode information, e.g., a specific allele for a polymorphic DNA sequence. The information can be detected using different reporter moieties, e.g., different colors of fluorophors. In some embodiments, the third oligonucleotide is detected using enzyme-based chemiluminescence or fluorogenic amplification.

In some embodiments, the method is used to analyze a genetic even, e.g., a SNP or a mutation. The genetic event can occur in the first region, the second region, or at the junction of the two regions.

In some embodiments, a biallelic or multi-allelic SNP is analyzed.

In some embodiments, the third oligonucleotides from a plurality of sites are analyzed.

In some embodiments, the third oligonucleotide is further amplified, e.g., by an isothermal method, prior to hybridization to the capture probe array. The amplification can include, e.g., rolling circle amplification (RCA). When RCA is used, the method can include:

(a) annealing an effective amount of the third oligonucleotide to a single-stranded circular template to yield an annealed circular template, wherein the single-stranded circular template comprises (i) at least one copy of a nucleotide sequence complementary to the sequence of the third oligonucleotide and optionally, (ii) at least one nucleotide effective to produce a cleavage site in an oligonucleotide multimer;

(b) providing the primed circular template with effective amounts of a primer, at least two types of nucleotide triphosphates and a polymerase enzyme, to yield a single-stranded oligonucleotide multimer complementary to the circular oligonucleotide template, wherein the oligonucleotide multimer comprises multiple copies (amplified) of the sample sequence; optionally, (c) cleaving the oligonucleotide multimer at the cleavage site to produce the cleaved amplified sample nucleic acid; and (d) hybridizing the cleaved sample nucleic acid to the array of capture probes.

In some embodiments, the method is used to detect single nucleotide polymorphisms (SNPs). Two different probes can be encoded with different tag sequences. Multiple pairs of signal probes can be used simultaneously with the same sample to multiplex the analysis of many target sequences. The products of the reaction can then be analyzed on a capture probe array, e.g., a PSBH array.

Methods of the invention also allow for capture of single stranded products form multiplexed PCR. Accordingly, in another aspect, the invention includes a method of analyzing a polynucleotide sequence. The method includes:

providing a double-stranded nucleic acid sequence, wherein the 5' ends of one or both sequences have a region of unique sequence;

(optionally) contacting the double-stranded nucleic acid sequence with an agent which promotes strand separating, e.g., a peptide-nucleic acid (PNA) having a sequence, e.g., a genetic sequence, complementary to a region near the end or ends of the double-stranded nucleic acid molecule, thereby exposing a region of single-stranded nucleic acid sequence containing the unique sequence; and hybridizing the nucleic acid sequence having an exposed single-stranded region to a capture array, thereby analyzing the nucleic acid sequence.

In some embodiments, the hybridized nucleic acid sequence is ligated to the capture array. Preferably, ligation is followed by a washing step.

In some embodiments, the method includes providing a pair of primers, e.g., PCR primers, having generic tags and peptide nucleic acid (PNA)-binding sites and using the primers to amplify the nucleic acid sequence. PNA are discussed in detail in Kuhn et al. J. Mol. Evol. 286:1337–1345 (1999) and Bukanov et al., Proc. Nat. Acad. Sci. (USA) 95:5516–20 (1998).

Methods of the invention can be used to capture unamplified genomic targets and analyze them in an array. Accordingly, in another aspect, the invention features a method of detecting a nucleic acid sequence. The method includes:

providing a population of double-stranded molecules having a defined sequence adjacent to at least one of their ends, wherein the defined sequences have a first and second defined regions, separated by a unique sequence region;

(optionally) opening the duplex at one end, e.g., by contacting the double-stranded molecules with a first and second peptide nucleic acid complementary to the first and second defined regions under conditions sufficient to cause the unique sequence region to become single-stranded; and hybridizing the double-stranded molecules having the single-stranded unique sequence region to a capture probe array, thereby analyzing the polynucleotide sequence.

In some embodiments, the double-stranded nucleic acid sequences are generated by digestion with a restriction enzyme.

In some embodiments, the single-stranded unique region is annealed with a primer having an arbitrary sequence tags at its 5' end. The annealed primer is then extended with a DNA polymerase and other reagents known in the art. If desired, the extended strand is further amplified using PCR or the RCA amplification methods described herein.

In some embodiments, the products of the primer extension or amplification are ligated to the capture probe arrays after hybridization. Preferably, the fragments are washed after ligation. The ligated capture probes can be further analyzed, e.g., by in situ RCA.

In some embodiments, the capture probes have 5' overhangs.

In some embodiments, the single-strand unique sequence region is hybridized with an oligonucleotide.

In another aspect, the invention includes a method of thereby analyzing a nucleic acid sequence. The method includes:

providing double-stranded fragments, e.g., genomic fragments, having at least one defined end, produced, e.g., by restriction digestion;

denaturing an end of a fragment, e.g., by contact with a peptide nucleic acid to produce an open end;

hybridizing a primer to the open end and extending it;

hybridizing the extension produces to a capture probe array, thereby analyzing a nucleic acid sequence.

In some embodiments, the primer has a generic sequence tag, e.g., at its 5' end, which can be hybridized to a capture probe, e.g., a PSBH array.

In some embodiments, the nucleic acid sample is unamplified genomic DNA.

In some embodiments, the products of the primer extension or amplification are ligated to the capture probe arrays after hybridization. Preferably, the fragments are washed after ligation. The ligated capture probes can be further analyzed, e.g., by in situ RCA.

In some embodiments, the capture probes have 5' overhangs.

In some embodiments, the single-strand unique sequence region is hybridized with an oligonucleotide.

The invention also features bifunctional oligonucleotide probes and methods of their use. Accordingly, in another aspect, the invention includes a method for analyzing a nucleic acid sequence. The method includes:

providing a population of single-stranded nucleic acid molecules, e.g., denatured genomic DNA;

contacting the population of nucleic acid molecules with an oligonucleotide to form a partially duplex region on the single-stranded nucleic acid molecules, wherein the oligonucleotide has a first region complementary to a defined nucleic acid sequence and a second region containing a recognition sequence for a type IIS restriction enzyme, e.g., Fok I;

cleaving the partially duplex region with the type IIS restriction enzyme, wherein the restriction enzyme cleaves in the first region of the oligonucleotide to form a oligonucleotide digestion product; and hybridizing the oligonucleotide digestion product to a capture probe array, thereby analyzing the nucleic acid sequence.

In some embodiments, the hybridized product is ligated to a capture probe array.

The invention also features hybrid generic/custom dual probe arrays and methods of their use. Accordingly, in another aspect, the invention features a method for analyzing a nucleic acid sequence. The method includes:

providing an array comprising a plurality of capture probes having a single-stranded region and a double-stranded region, wherein preferably the plurality of capture probes includes a generic capture probe and a custom capture probe.

hybridizing a sample nucleic acid to the array, wherein the hybridizing sample nucleic acid binds to a single-stranded region in a capture probe in the array so that the 5' terminus of the sample nucleic acid abuts the 3' terminus of the double-stranded region of the capture probe; and ligating the sample nucleic acid to the 3' terminus of the double-stranded region of the capture probe.

In some embodiments, the sample nucleic acid is labeled, e.g., with biotin, a fluorophore, or one or more radiolabeled nucleotides.

In some embodiments, the 3' terminus of the sample nucleic acid is extended using a DNA polymerase and sequences in the single stranded region of the capture probe as the template.

In some embodiments, the extended product is labeled, e.g., with biotin, a fluorophore, or one or more radiolabeled nucleotides.

The invention also features creation of custom arrays by hybridization of probe pools. Accordingly, in another aspect, the invention includes a method for forming a custom array. The method includes:

providing an array of a plurality of foundation probes, wherein each of the foundation probes is positionally distinguishable from other foundation probes of the plurality on the array and wherein each of the foundation probes contains a region of unique sequence;

contacting the foundation probe array with a plurality of custom oligonucleotides comprising a first and second sequence, wherein the first sequence is complementary to a defined sequence in a foundation probe in the foundation probe array and the second sequence is complementary to a target sequence, thereby forming a custom probe array.

In some embodiments, the 5' end of the oligonucleotide abuts the 3' end of a nucleotide in the foundation probe array.

In some embodiments, the oligonucleotide can be ligated to the foundation probe array.

In some embodiments, a sample of nucleic acids is hybridized to the capture probe array and nucleic acids in the sample which hybridize to the second sequence in the oligonucleotide are identified. In some embodiments, the 3' terminus of the hybridizing sample nucleic acid is extended using a DNA polymerase and sequences in the capture probe array as a template.

In some embodiments, the sample nucleic acids are labeled.

The invention also features a kit for analyzing a sample of nucleic acid molecules.

The array includes:
a foundation probe array comprising foundation probes having a defined sequence;
an oligonucleotide comprising a first and second sequence, wherein the first sequence is complementary to a defined sequence in a foundation probe in the foundation probe array and the second sequence is complementary to a target sequence.

Methods of the invention can also be used to capture RCA products containing multiplex tags. Accordingly, in one aspect, the invention includes a method of analyzing a polynucleotide, e.g., detecting a genetic event, e.g., a single nucleotide polymorphism, in a sample. The method includes:

providing a sample which includes a sample polynucleotide sequence to be analyzed;
(2) (a) annealing an effective amount of sample sequence to a single-stranded circular template to yield an annealed circular template, wherein the single-stranded circular template comprises (i) at least one copy of a nucleotide sequence complementary to the sequence of the sample sequence and optionally, (ii) at least one nucleotide effective to produce a cleavage site in an oligonucleotide multimer;

(b) providing the primed circular template with effective amounts of a primer, at least two types of nucleotide triphosphates and a polymerase enzyme, to yield a single-stranded oligonucleotide multimer complementary to the circular oligonucleotide template, wherein the oligonucleotide multimer comprises multiple copies (amplified) of the sample sequence; optionally, (c) cleaving the oligonucleotide multimer at the cleavage site to produce the cleaved amplified sample nucleic acid; and (3) analyzing the sample sequence from (2) (b) or (c), e.g., by providing an array of a plurality of capture probes, wherein each of the capture probes is positionally distinguishable from other capture probes of the plurality on the array, and wherein each positionally distinguishable capture probe of the plurality includes a unique (i.e., not repeated in another capture probe) region; and hybridizing the amplified sample sequence with the array of capture probes, thereby analyzing the sample sequence.

In preferred embodiments, the amplified sequence from step 2 of the method can be further amplified, e.g., amplified by rolling circle, e.g., prior to analysis under step 3. In such embodiments, the amplified sample nucleic acid from step 2, e.g., a cleaved amplified sample nucleic acid, can be amplified further. The second or other subsequent rolling circle amplification can use a circular oligonucleotide probe of the same or similar sequence that used as Step 2, or one of a different sequence. It is also possible that the circular oligonucleotide in a second or subsequent rolling circle amplification, can be, for example, closed or open circular template.

In preferred embodiments, the circular oligonucleic template (of any step) is prepared by a process comprising the steps of:

(a) hybridizing each end of a linear precursor oligonucleotide to a single positioning oligonucleotide, e.g., a sample sequence, having a 5' nucleotide sequence complementary to a portion of the sequence comprising the 3' end of the linear precursor oligonucleotide and a 3' nucleotide sequence complementary to a portion of the sequence comprising the 5' end of the linear precursor oligonucleotide, to yield an open oligonucleotide circle wherein the 5' end and the 3' end of the open circle are positioned so as to abut each other; and (b) joining the 5' end and the 3' end of the open oligonucleotide circle to yield a circular oligonucleotide template. Rolling circle amplification can be primed by the positioning oligonucleotide, e.g., the target nucleic acid, or by another primer, in this or other methods disclosed herein.

In preferred embodiments, analyzing a nucleic acid includes, e.g., sequencing the nucleic acid, e.g., by sequencing by hybridization or positional sequencing by hybridization, detecting the presence of, or identifying, a genetic event, e.g., a SNP, in a target nucleic acid, e.g., a DNA.

In preferred embodiments, the genetic event is within 1, 2, 3, 4 or 5 base pairs from the end of the target molecule, or is sufficiently close to the end of the target molecule that a mismatch would inhibit DNA polymerase-based extension from a target/primed circle. In preferred embodiments the inhibition is at least 50, 75, 90 or 99%.

In preferred embodiments, the target is amplified, e.g., by a isothermal or nonisothermal method, e.g., by PCR, prior to contact with a circular template.

In preferred embodiments the circular template includes a site for a type IIS restriction enzyme and the site is positioned, e.g., such that a type IIS restriction binding at the site cleaves adjacent the region which binds the sample sequence or cleaves in the region which binds the sample sequence.

In a preferred embodiment a region of the circular template is complementary to a genetic event, e.g., a mutation or SNP, and hybridizes effectually to sample nucleic acid having the event and sample nucleic acid not having the event.

In preferred embodiments, each of the capture probes has a binding region for a non-specific endonuclease binding site, e.g., a type IIS restriction enzyme binding site, and the method includes:

hybridizing the single stranded target nucleic acid with the capture probe array, (preferably the region of an amplification product which corresponds to the genetic event hybridizes with the variable region of a capture probe);

(optionally) ligating the single stranded target nucleic acid to a strand of the capture probe;

cleaving the single stranded target nucleic acid/capture probe duplex with a non-specific endonuclease, to form a cleaved single stranded target nucleic acid/capture probe duplex, such that a base corresponding to the genetic event is in the single stranded region formed by the cleavage;

extending along the single strand which contains the genetic event with one and preferably with 2, 3, or all 4 labeled chain terminating nucleotides, wherein if more than one labeled chain terminating nucleotide is used each of the chain terminators, e.g., A or C, are distinguishable, such that the incorporation of a chain terminator indicates the presence of a genetic event.

thereby detecting or identifying a genetic event in a target nucleic acid.

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments hybridization to the array is detected by mass spectrophotometry, e.g., by MALDI-TOF mass spectrophotometry.

In preferred embodiments probes are selected for minimal cross hybridization with other probes.

In preferred embodiments the amplified sample sequence has attached thereto a first member of a proximity detector pair and hybridization to the array allows the first member to be brought into proximity with a second member to provide a signal.

In a preferred embodiment the amplified sample sequence which hybridizes to a capture probe, or the capture probe, is the substrate of or template for an enzyme mediated reactions. For example, after hybridization to the capture probe, the amplified sample sequence is ligated to the capture probe, or after hybridization it is extended along the capture probe.

In preferred embodiments the method includes one or more enzyme mediated reactions in which a nucleic acid used in the method, e.g., an amplified sample sequence, a capture probe, a sequence to be analyzed, or a molecule which hybridizes thereto, is the substrate or template for the enzyme mediated reaction. The enzyme mediated reaction can be: an extension reaction, e.g., a reaction catalyzed by a polymerase; a linking reaction, e.g., a ligation, e.g., a reaction catalyzed by a ligase; or a nucleic acid cleavage reaction, e.g., a cleavage catalyzed by a restriction enzyme, e.g., a Type IIS enzyme. The amplified sample sequence which hybridizes with the capture probe can be the substrate in an enzyme mediated reaction, e.g., it can be ligated to a strand of the capture probe or it can be extended along a strand of the capture probe. Alternatively, the capture probe can be extended along the hybridized amplified sample sequence. (Any of the extension reactors discussed herein can be performed with labeled, or chain terminating, subunits.) The capture probe duplex can be the substrate for a cleavage reaction. These reactions can be used to increase specificity of the method or to otherwise aid in detection, e.g., by providing a signal.

Methods such as those described in U.S. Pat. No. 5,503,980 or 5,631,134, both of which are hereby incorporated by reference, can be used in methods of the invention. In particular, the array and array-related steps recited herein can use methods taught in these patents.

In preferred embodiments, the method includes: providing an array having a plurality of capture probes, wherein each of the capture probes is a) positionally distinguishable from the other capture probes of the plurality and has a unique variable region (not repeated in another capture probe of the plurality), b) has a variable region capable of hybridizing adjacent to the genetic event; and c) has a 3' end capable of serving as a priming site for extension hybridizing the amplified sample sequence having a genetic event to a capture probe of the array, (preferably the region of the amplified sample sequence having a genetic event hybridizes adjacent to the variable region of a capture probe); and using the 3' end of the capture probe to extend across the region of genomic nucleic acid having a genetic event with one or more terminating base species, where if more than one is used each species has a unique distinguishable label e.g. label 1 for base A, label 2 for base T, label 3 for base G, and label 4 for base C; thereby analyzing the amplified sample sequence.

The nucleic acids, e.g., probes and primers, arrays, and other reagents or devices disclosed herein are also within the invention.

In another aspect, the invention features a probe, e.g., a probe described herein, which is useful for rolling circle amplification. The probe includes, preferably in the order of 5' to 3':

a first region at one terminus of the probe, which includes a sequence which hybridizes to a first region of a target nucleic acid sequence;

a second region which includes a cleavage site, e.g., a site for cleavage by a restriction enzyme sequence, e.g., a type IIs enzyme and a capture tag sequence;

a third region which includes a sequence complementary to a universal primer sequence; and a fourth region, at the other terminus of the probe, which includes a sequence which hybridizes to a second region of a target sequence.

The total length of the probe can range, e.g., between 10 to 500 nucleotides. In one example, the first region of the probe can range in length from between about 9 to 50, or between 10–15 nucleotides in length. The capture tag sequence within the second region of the primer can range in length between 2–100, preferably 4–20, more preferably 4–12 and most preferably 4–8 and 6–8 nucleotides in length. The cleavage site within the second region can range between 5–40 nucleotides in length. The third region of the sequence can range between 6–100, preferably 7–50, more preferably 9–30 and most preferably 10–25 and 12–20 nucleotides in length. The fourth region of the primer can range in length from between about 9 to 50, or between 10–15 nucleotides in length.

Capture tag sequences should be designed to minimize secondary structure and to promote efficient hybridization, e.g., to an array of capture probes. In preferred embodiments a capture tag is a sequence not found at a terminus, and more preferably not found in the target sequence. A sequence complementary to the universal primer should be designed such that the universal primer can hybridize to and direct the amplification of a target nucleic acid sequence.

The invention also features, a plurality of rolling circle amplifying probes (a set of probes), wherein each probe of the plurality of probes includes a unique capture tag sequence. An integration site nucleotide can differ between pairs, e.g., a plurality can include pairs with 2, 3, or all of a, g, c, t as an interrogation site nucleotide.

The total length of the primer can range between 10 to 400 nucleotides. In one example, the first region of the probe can range in length from between about 9 to 30, or between 10–15 nucleotides in length. The capture tag sequence within the second region of the probe can range in length between 2–100, preferably 4–20, more preferably 4–12 and most preferably 4–8 and 6–8 nucleotides in length. The cleavage site can range between 5–40 nucleotides in length. The third region of the sequence can range between 6–100, preferably 7–50, more preferably 9–30 and most preferably 10–25 and 12–20 nucleotides in length. The fourth region of the probe can range in length from between about 9 to 50, or between 10–15 nucleotides in length.

Each probe in the plurality should include a unique capture tag sequence so as to allow separate analysis. Thus, the capture tags will differ by at least 1 and preferably at at least 2, 3, 4, 5, 6, 10, or 20 nucleotides. In preferred embodiments the sequence of capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences.

The probes can be used to detect a genetic event, e.g., a mutation or an SNP, in a target sequence. The nucleotide complementary to the genetic event or to a nucleotide of a genetic event, can be degenerate in the plurality. The plurality of probes can differ from each other at the end terminus of the probe. The probes should include at their interrogation site, or at the end close to their interrogation site a degenerate nucleotide which allows for ligation or polymerase extension, only when hybridized to a specific target.

The invention also features a pair of primers/probes, e.g., PCR primers, which allow for the extension, e.g., amplification, of a particular nucleotide sequence. Accordingly, the invention features a pair of primers including:

(a) a first primer which includes, preferably in the order of 5' to 3':

a first region which includes a sequence complementary to a universal primer sequence;

a second region which includes a cleavage site, e.g., a site for cleavage by a restriction enzyme sequence, e.g., a type IIs enzyme and a capture tag sequence, wherein the capture sequence has preferably a different sequence than any other capture sequence;

a third region which includes a sequence which hybridizes to a first target sequence; and (b) a second primer which includes, preferably in the order of 5' to 3':

a first region which includes a sequence complementary to a universal primer sequence;

a second region which includes a cleavage site, e.g., a site for cleavage by a restriction enzyme sequence, e.g., a type IIs enzyme and a capture tag sequence, wherein the capture sequence has the same or different sequence than the capture sequence of the first primer; and a third region which includes a sequence which hybridizes to a second target sequence.

The total length of the primer can range between 10 to 200 nucleotides. In one example, the first region of the primer can range in length from between about 9 to 30, or between 10–15 nucleotides in length. The capture tag sequence within the second region of the primer can range in length between 2–100, preferably 4–20, more preferably 4–12 and most preferably 4–8 and 6–8 nucleotides in length. The cleavage site can range between 5–40 nucleotides in length. The third region of the sequence can range between 6–100, preferably 7–50, more preferably 9–30 and most preferably 10–25 and 12–20 nucleotides in length.

Each probe in the plurality should include a unique capture sequence tag so as to allow separate analysis. Thus, the capture tags will differ by at least 1 and preferably at least 2, 3, 4, 5, 6, 10, or 20 nucleotides. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences.

In one embodiment, the target sequences can be different regions on the same molecule. In another embodiment, the target sequences can be on different molecules.

The invention also features a plurality (or set) of pairs of primers, e.g., PCR primers, wherein each pair of the plurality includes a unique sequence tag. An integration site nucleotide can differ between pairs, e.g., a plurality can include pairs with 2, 3, or all of a, g, c, t as an interrogation site nucleotide.

The total length of the primer can range, e.g., between 10 to 500 nucleotides. In one example, the first region of the primer can range in length from between about 9 to 30, or between 10–15 nucleotides in length. The capture tag sequence within the second region of the primer can range in length between 2–100, preferably 4–20, more preferably 4–12 and most preferably 4–8 and 6–8 nucleotides in length. The cleavage site can range between 5–40 nucleotides in length. The third region of the sequence can range between 6–100, preferably 7–50, more preferably 9–30 and most preferably 10–25 and 12–20 nucleotides in length.

A capture tag sequence in each pair of the plurality of pairs should each be unique so as to allow separate analysis. Thus, the capture tags will differ by at least 1 and preferably at at least 2, 3, 4, 5, 6, 10, or 20 nucleotides. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences. In a pair of probes the capture tag sequences can differ or they can be identical.

The probes can be used to detect a genetic event, e.g., a mutation or an SNP, in a target sequence. The nucleotide complementary to the genetic event or to a nucleotide of a genetic event, can be degenerate in the plurality. The plurality of probes can differ from each other at the end terminus of the probe. The probes should include at their interrogation site, or at the end close to their interrogation site a degenerate nucleotide which allows for ligation or polymerase extension, only when hybridized to a specific target.

The invention also features a pair of primers/probes, e.g., ligation or PCR primers, which allow for the extension, e.g., amplification, of a particular nucleotide sequence including:

(a) a first primer in the order of 5' to 3' having:
  a first region which includes a sequence complementary to a universal primer sequence;
  a second region which includes a capture tag sequence, wherein the capture sequence has preferably a different sequence than any other capture sequence, and a cleavage site, e.g., a site for cleavage by a restriction enzyme sequence, e.g., a type IIs enzyme;
  a third region which includes a sequence which hybridizes to a first target sequence; and (b) a second primer in the order of 5' to 3' having:
  a first region which can hybridize to a second region on the target nucleic acid sequence;
  a second region which includes a capture tag sequence, wherein the capture sequence has preferably a different sequence than any other capture sequence, and a cleavage site, e.g., a site for cleavage by a restriction enzyme sequence, and
  a third region which includes a sequence complementary to a universal primer sequence.

The total length of the primer can range between 10 to 200 nucleotides. In one example, the first region of the primer can range in length from between about 9 to 30, or between 10–15 nucleotides in length. The capture tag sequence within the second region of the primer can range in length between 2–100, preferably 4–20, more preferably 4–12 and most preferably 4–8 and 6–8 nucleotides in length. The cleavage site can range between 540 nucleotides in length. The third region of the sequence can range between 6–100, preferably 7–50, more preferably 9–30 and most preferably 10–25 and 12–20 nucleotides in length.

A capture tag sequence in each primer should each be unique so as to allow separate analysis. Thus, they will differ by at least 1 and preferably at least 2, 3, 4, 5, 6, 10, or 20. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences.

In one embodiment, the target sequences can be different regions on the same molecule. In another embodiment, the target sequences can be on different molecules.

The invention also features a plurality of pairs of primers, e.g., ligation or PCR primers, which allow for the extension, e.g., amplification, of a set of target nucleotide sequences, wherein each of the pairs includes a unique sequence tag. An integration site nucleotide can differ between pairs, e.g., a plurality can include pairs with 2, 3, or all of a, g, c, t as an interrogation site nucleotide.

The total length of the primer can range, e.g., between 10 to 500 nucleotides. In one example, the first region of the primer can range in length from between about 9 to 30, or between 10–15 nucleotides in length. The capture tag sequence within the second region of the primer can range in length between 2–100, preferably 4–20, more preferably 4–12 and most preferably 4–8 and 6–8 nucleotides in length. The cleavage site can range between 5–40 nucleotides in length. The third region of the sequence can range between 6–100, preferably 7–50, more preferably 9–30 and most preferably 10–25 and 12–20 nucleotides in length.

Each pair should include a unique capture tag sequence so as to allow separate analysis. Thus, they will differ by at least 1 and preferably at at least 2, 3, 4, 5, 6, 10, or 20. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences. In a pair of probes the capture tag sequences can differ or they can be identical.

In one embodiment, the target sequences can be different regions on the same molecule. In another embodiment, the target sequences can be on different molecules.

The probes can be used to detect a genetic event, e.g., a mutation or an SNP, in a target sequence. The nucleotide complementary to the genetic event or to a nucleotide of a genetic event, can be degenerate in the plurality. The plurality of probes can differ from each other at the end terminus of the probe. The probes should include at their interrogation site, or at the end close to their interrogation site a degenerate nucleotide which allows for ligation or polymerase extension, only when hybridized to a specific target.

The invention also features a pair of probes for invader-directed cleavage, wherein the invader-directed cleavage pair includes:
 (a) an invader probe including a region which hybridizes to a first region on the target sequence; and
 (b) a signal probe including, preferably in the order of 5' to 3' including:
  optionally a signal sequence;
  a capture tag sequence; and
  a region which can hybridize to a second region on the target nucleic acid sequence.

The total length of the probe can range between 10 to 400 nucleotides. In one example, the capture tag sequence probe can range in length between 2–100, preferably 4–20, more preferably 4–12 and most preferably 4–8 and 6–8 nucleotides in length.

The capture tag sequences in the plurality of the probes should each be unique so as to allow separate analysis. Thus, they will differ by at least 1 and preferably at at least 2, 3, 4, 5, 6, 10, or 20. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences. In a pair of probes the capture tag sequences can differ or they can be identical.

In one embodiment, the target sequences can be different regions on the same molecule. In another embodiment, the target sequences can be on different molecules.

The invention also features a plurality of pairs of probes for the invader-directed cleavage, wherein each pair of the plurality includes a unique sequence tag. An integration site nucleotide can differ between pairs, e.g., a plurality can include pairs with 2, 3, or all of a, g, c, t as an interrogation site nucleotide.

The total length of the probes can range between 10 to 400 nucleotides. The capture tag sequence can range in length between 2–100, preferably 4–20, more preferably 4–12 and most preferably 4–8 and 6–8 nucleotides in length. The cleavage site can range between 5–40 nucleotides in length. The third region of the sequence can range between 6–100, preferably 7–50, more preferably 9–30 and most preferably 10–25 and 12–20 nucleotides in length.

Each probe of the plurality should include a unique capture tag sequence so as to allow separate analysis. Thus, capture tags will differ by at least 1 and preferably at at least 2, 3, 4, 5, 6, 10, or 20 nucleotides. In preferred embodiments the sequence of the capture tag in each of the plurality of probes will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of probes which amplify the sense and antisense strand of a target can have the same or different capture tag sequences. In a pair of probes the capture tag sequences can differ or they can be identical.

In one embodiment, the target sequences can be different regions on the same molecule. In another embodiment, the target sequences can be on different molecules.

The invention further includes the derivative nucleic acid sequences or the plurality of derivative nucleic acid sequences described herein. For example, the invention includes the derivative nucleic acid sequence including one or more capture tags and a target nucleic acid sequence, and optionally a signal molecule. Preferably, the capture tag is at one or both of the ends of the nucleic acid sequence. In one example, the nucleic acid sequence is a double stranded molecule including a 3' overhang which includes the capture tag. In another example, the nucleic acid sequence is a double stranded molecule including a 5' overhang which includes the capture tag. In yet another example, the nucleic acid is a single stranded sequence including a capture probe at its 5' and 3' termini.

A capture tag sequence is a sequence which allows identification of the probe or derivative nucleic acid of which it is a part. A capture tag sequence is preferably 2–100, more preferably 4–20, more preferably 4–12, and most preferably 4–8 or 6–8, nucleotides in length. Probes or derivative nucleic acids which include capture tags are generally used in sets, i.e., more than one is used, so that multiplexed analysis can be performed. The sequence of capture tags on the molecules of a set should each be unique so as to allow separate analysis. Thus, they will differ at at least 1 and preferably at at least 2, 3, 4, 5, 6, 10, or 20. In preferred embodiments the sequence of the capture tag in each molecule of a set will be sufficiently different that a sequence tag will not hybridize, under assay conditions used, to a sequence which is complementary to another capture tag in the set, in other words, they will not cross hybridize. Capture tag sequences can also be designed to minimize secondary structure, to promote efficient hybridization, e.g., to an array of capture probes. In preferred embodiments a capture tag is a sequence not found at a terminus, and more preferably not found in the target sequence. A set of primers which amplify the sense and antisense strand of a target can have the same or different capture tag sequences.

A universal primer is one which can hybridize to and direct the amplification of a plurality of different nucleic acids, e.g., a plurality of different derivative nucleic acids of a plurality of nucleic acids having different capture tags.

A derivative nucleic acid is a nucleic acid which includes a capture tag sequence at one or both of its termini in a single strand overhang. The derivative sequence is produced only upon the hybridization of a probe, which include the sequence tag as an internal fragment, to the target sequence for which it is specific.

The invention provides methods for the multiplexed analysis of complex mixtures of nucleic acids by the generation and capture of a plurality of species of derivative nucleic acid molecules, the generation of which is dependent on the presence of specific nucleic acid molecules in a sample. A plurality of derivative nucleic acid molecules is generated for each species of target nucleic acid molecule to be analyzed in the sample. The nucleic acid sequences at one terminal region of the derivative nucleic acid molecules are "arbitrary" tag sequences that are present initially as internal sequences in probes used to prepare the derivative nucleic acids. The derivative nucleic acid molecules are analyzed, e.g., captured and sorted by contiguous base stacking hybridization of their terminal tag regions to single-stranded overhangs of a plurality of spatially separated partially duplex probes. Hybridization of the tag sequences on the derivative nucleic acid molecules to the partially duplex probes is very specific due to the use of an optimized set of relatively short sequences in the single-stranded overhangs. The specificity may be enhanced by a requirement for ligation or polymerization reactions for successful capture. The invention is useful for sorting or demultiplexing the products of multiplexed amplification reactions or assays on microarrays or beads.

Preferred embodiments feature tag sequences which are not found in the target nucleic acid sequences. This results in a more efficient, more specific assay, particularly when the tags in a reaction are chosen so as to minimize cross hybridization, i.e., hybridization of a first tag to a sequence complementary to a second tag. As the sequence tags need not and preferable are not able to hybridize to the tags under conditions under which the assay is performed, they can be tailored to provide efficient specific hybridization, e.g., to a capture array.

The capture tags used in methods of the invention are initially supplied as internal sequences, i.e., they are flanked on both sides with other sequences. Only after a target sequence specific reaction are tags found at the terminus of a nucleic acid. The internal positioning makes it very difficult for un-reacted tag-containing probes to hybridize to a capture probe. On the contrary, reacted molecules, which present the tag sequence at a terminus, hybridize readily with capture probes, particularly partially duplex probes having a single strand over hang which is complementary with a tag sequence.

Methods of the invention are useful for many applications including quantification of the expression levels of specific genes, detection of the allelic variants of multiple polymorphic sites within individuals, screening for genetic disease, pharmacogenomic analysis to optimize drug therapy, detection of infectious agents and variants of these agents, and forensic analysis to identify human or animal species or individuals.

Methods described herein provide for the multiplexed amplification and/or analysis of nucleic acid target sequences by the specific capture of molecules that are derived from probe molecules ("target-specific probes") that interact with target molecules and that are encoded with tag sequences unrelated to the target sequences. The tag sequences are initially present internally in the target-specific probes. As a result of specific interaction of the target-specific probes with the nucleic acid target molecules, these tag sequences will be present at the termini of molecules derived from the target-specific probes ("derivative nucleic acids").

The enhanced discrimination of partially duplex probes is exploited for the highly specific capture and sorting of the derivative nucleic acids. Target-specific probe molecules that have not interacted in specific ways with target sequences are not captured since the sequence tags are not present on their termini. Thus the microarrays of generic probes are used to effectively demultiplex multiplexed solution phase reactions that produce derivative nucleic acids.

Partially duplex arrays can be used in two ways: 1) to capture and sort amplified target sequences resulting from multiplexed amplification reactions such as PCR or RCA, and 2) to capture and sort the reaction products of multiplexed assays such as Invader assays.

Derivative nucleic acid can be partitioned by specific hybridization and immobilized by sequence specific-recognition onto an array element containing oligonucleotide(s) packaged into a device. Each array element can specifically capture cleaved fragments arising from a single initial recognition event representing the target nucleic acid in the original sample. The signal intensity detected at each element can then reflect the relative abundance of the target molecule relative to other nucleic acid targets or alleles in the original sample. Thus, a multitude of array elements can capture a multitude of cleaved fragment species.

Methods of the invention provide for multiplexing nucleic acid amplification and detection processes. This allows for the simultaneous analysis of a large number of nucleic acid fragments present in the sample. In the final detection step, a specific quantitative signal is detected for each allele or nucleic acid fragment present in the sample. Spatial separation of the amplification targets into distinct array elements eliminates competition of simultaneously amplifying targets and improves the fidelity and yield of the overall process. Further, the spatial separation provides a direct means of marking amplification targets that yield insufficient or no signals due to failed amplification reactions that potentially arise from failure of priming events or mispriming. These steps minimize generation of ambiguous data and facilitates troubleshooting attempts.

Also described are a variety of detection methods for qualitative and quantitative determination of each nucleic acid or allele present in the sample. Detection methods can rely on, e.g., fluorescent signals, redox pairs, electronic detection, or enzymatic reactions.

Devices for miniaturization and parallel analysis of nucleic acids in a sample can include, e.g., microplates, acrylamide gel pads, flow-through chips, and or other supports.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Description of Figures

FIG. 3 is a diagram of the elements of 5' and 3' probe/primers that are ligatable to a specific nucleic acid sequence and that can be amplified by PCR with universal primers.

Partially Duplex Capture Probes

Figure 1:
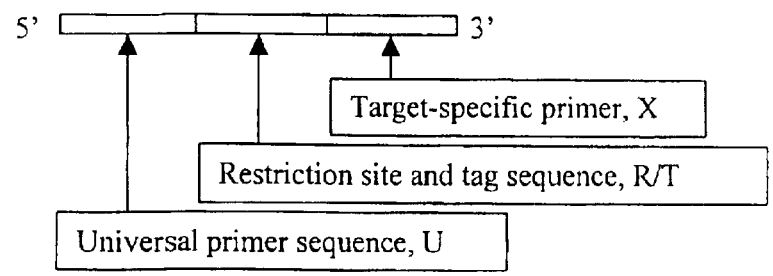
FIG. 1 is a diagram of the elements of primer adapters for multiplex PCR amplification with universal primer sequences and the capture and sorting of the derivative nucleic acids on partially duplex arrays.

Methods disclosed herein are performed with a plurality of partially duplex probes, each with a unique sequence in its region of single-stranded overhang. The overhangs may be 3' or 5' overhangs, depended on the type of molecule that is to be captured.

The partially duplex probes may be formed from two nucleic acid segments that are covalently linked and which form a partially self-complementary hairpin structure (see, e.g., U.S. Pat. No. 5,770,365, hereby incorporated by reference). A chemical moiety such as an amine group may be present on the partially duplex probe, preferably on the loop region of the hairpin, to effect covalent immobilization to a substrate.

The partially duplex probes may also be formed from two nucleic acid segments that are bound by non-covalent interactions, e.g., by hydrogen bonding of complementary base pairs. A chemical moiety such as an amine group may be present somewhere on one of the nucleic acid segments to effect covalent immobilization to a substrate. It is preferred that the binding of the two nucleic acid segments be adequately stable so that they form stable complexes in solution, and hence may be utilized as a preformed reagent. Making the regions of complementary long enough to be stable at the temperatures and solution conditions in which they will be used will effect stable interactions between the segments. Incorporation of nucleic acid analogs such as peptide nucleic acids that enhance the stability of nucleic acid hybrids will also enhance the stability of the complexes. Attaching binding moieties to the segments can also be used to effect stable interactions between the segments. For example, biotin can be added to each of the segments, and the segments can be combined in approximately equimolar amounts and allowed to form hybrids in solution. A dimeric antibody to biotin can then be added to stabilize the hybrid. The antibody can also be used to immobilize the partially duplex probe.

In one preferred embodiment the partially duplex probes are immobilized on positionally distinguishable elements of a microarray, which may be created on a non-porous substrate or on a three dimensional porous substrate. The three dimensional porous substrate may consist of a hydrophilic polymer matrix, such as derivatized polyacrylamide, to which the probes are covalently attached.

In another preferred embodiment the partially duplex probes are immobilized on different beads that may be distinguished by an analytical means such the spectral properties of electromagnetic absorption or fluorescence emission.

The single-stranded overhangs on the partially duplex probes may be from four the twenty bases long. A set of single stranded probe sequences is selected from all the possible sequences in the overhangs—e.g., 1024 for five base overhangs or 4096 for six base overhangs. Probe sequences are selected to provide highly specific and efficient capture with minimal cross-reaction between the probes. The sequences of the single-stranded probe overhang sequences are unrelated to target sequences in the samples to be analyzed. Rather, the overhang sequences are complementary to the capture tag sequences that are initially present internally in probe molecules ("target-specific probes") that interact with the target nucleic acids in solution. As a result of specific interaction of the target-specific probes with the nucleic acid target molecules, these tag sequences will be present at the termini of molecules derived from the target-specific probes ("derivative nucleic acids").

Suitable restriction enzymes for use in the invention are listed in the table below.

| Enzyme | Type of overhang | # bases in overhang |
|---|---|---|
| ApaBI | 3' | 5 |
| BaeI | 3' | 5 |
| Bbr7I | 5' | 4 |
| BplI | 3' | 5 |
| BsaI | 5' | 4 |
| BsmBI | 5' | 4 |
| Bsp24I | 3' | 5 |
| BstXI | 3' | 4 |
| BbvI | 5' | 4 |
| BsmAI | 5' | 4 |
| BsmFI | 5' | 4 |
| CjeI | 3' | 6 |
| CjePI | 3' | 6 |
| FokI | 5' | 4 |
| HaeIV | 3' | 6,5 |
| HgaI | 5' | 5 |

-continued

| Enzyme | Type of overhang | # bases in overhang |
|---|---|---|
| Sth132I | 5' | 4 |
| StsI | 5' | 4 |

Positional Arrays

Positional arrays suitable for the present invention include high and low density arrays on a two dimensional or three dimensional surface. Positional arrays include nucleic acid molecules, peptide nucleic acids or high affinity binding molecules of known sequence attached to predefined locations on a surface. Arrays of this nature are described in numerous patents which are incorporated herein by reference. These include, e.g., Cantor, U.S. Pat. No. 5,503,980; Southern, EP 0373 203 B1; Southern, U.S. Pat. No. 5,700,637 and Deugau, U.S. Pat. No. 5,508,169. The density of the array can range from a low density format, e.g., a microliter plate, e.g., a 96- or 384-well microliter plate, to a high density format, e.g. 1000 molecules/cm$^2$, as described in, e.g., Fodor, U.S. Pat. No. 5,445,934.

The surface on which the arrays are formed can be two dimensional, e.g., glass, plastic, polystyrene, or three dimensional, e.g. polymer gel pads, e.g. polyacrylamide gel pads of a selected depth, width and height.

In preferred embodiments, the target or probes bind to (and can be eluted from) the array at a single temperature. This can be effected by manipulating the length or concentration of the array or nucleic acid which hybridizes to it, by manipulating ionic strength or by providing modified bases.

Gel Pad Arrays

Array-based method described herein can be practiced on gel pad arrays. Gel pads, including arrays of gel pads, can be prepared by a variety of methods, some of which are known in the art. Examples of these methods are provided in, e.g., Timofeev et al., *Nucleic Acids Research* (1996), Vol. 24, 3142–3148; Drobyshev et al., *Gene* (1997) 188: 45–52; Livshits et al., *Biophysical Journal* (1996) 71:2795–2801; Yershov et al., *Proc. Natl. Acad. Sci.* USA (1996) 93:4913–4918; Dubiley et al., *Nucleic Acids Research* (1997), Vol. 25, 2259–2265; and U.S. Pat. No. 5,552,270 by Khrapko et al. Each of the foregoing is incorporated herein by reference. Gel pad arrays are the preferred positional arrays for use in the methods described herein.

In some embodiments, a sample which contains a target analyte, e.g., a polynucleotide, such as a sample which contains genomic DNA, is loaded into a gel pad. An array of gel pads on a first solid support can be employed to perform an analysis on a plurality of samples, or a plurality of probes to detect a plurality of characteristics, e.g., SNPs, of a sample or samples. The genomic DNA is preferably digested, e.g., with a restriction enzyme, to provide shorter fragments of DNA which can easily diffuse into the gel pad(s). The gel pad composition and/or the size of fragments can be selected to permit the target polynucleotides to diffuse into the gel pad, and/or to prevent larger pieces of, e.g., genomic DNA from diffusing into the gel pad. The volume of the gel pad(s) is preferably less than about 1 microliter, more preferably less than about 500, 100, 50, 10, 5, 1, 0.5, or 0.1 nanoliters per gel pad. Volumes in this range permit the diffusion of reactants and target to occur in a conveniently short time period (e.g., preferably less than 5, 2, 1, 0.5, or 0.1 minutes). After the sample polynucleotide has diffused into the gel pad, the remaining sample can be washed away.

An "array" can be any pattern of spaced-apart gel pads disposed on a substrate. Arrays can be conveniently provided in a grid pattern, but other patterns can also be used. In preferred embodiments, a gel pad array includes at least about 10 gel pads, more preferably at least about 50, 100, 500, 1000, 5000, or 10000 gel pads. In some embodiments, the array is an array of gel pads of substantially equal size, thickness, density, and the like, e.g., to ensure that each gel pad behaves consistently when contacted with a test mixture. In certain embodiments, however, the pads of a gel pad array can differ from one another; e.g., a mixed gel pad array can be constructed which includes more than one size or type of gel pad, e.g., gel pads made of different gel materials, or which entrap different species such as reagents or polynucleotide probes. In certain preferred embodiments, gel pads in an array are less than about 1 mm in diameter (or along a side, e.g., in the case of square gel pads), more preferably less than about 500 microns, still more preferably less than about 100, 75, 50, 25, 10, 5, or 1 micron in diameter.

A gel pad can have any convenient dimension for use in a particular assay. In preferred embodiments, a gel pad is thin enough, and porous enough, to permit rapid diffusion of at least certain reaction components into the gel pad when a solution or suspension is place din contact with the gel pad. For example, in one embodiment, a gel pad array for use in sequencing by hybridization permits polynucleotide fragments from a sample mixture to diffuse (within a conveniently short time period) into the gel pads and hybridize to oligonucleotide capture sequences disposed within the gel pads. In certain preferred embodiments, a gel pad (e.g., in an array of gel pads) has a thickness of at least about 1, 5, 10, 20, 30, 40, 50 or 100 microns. In certain preferred embodiments, a gel pad (e.g., in an array of gel pads) has a thickness of less than about 1 millimeter, 500 microns, 200, 100, 50, 40, 30, 20, 10, 5, or 1 microns.

In preferred embodiments, a first gel pad (or each the first array of gel pads) includes a first primer, e.g., a first PCR primer. The first primer is preferably complementary to at least a portion of the sample polynucleotide (or to its complement). The first primer is preferably immobilized in the first gel pad to prevent migration of the primer out of the gel pad. The immobilization can be permanent or reversible, and can be covalent or non-covalent.

EXAMPLE 1

Multiplex PCR with Two Target-Specific Primers Incorporating Universal Primer Sequences, Type IIS Restriction Sites and Generic Capture Tags, followed by Capture of One or Both Target Strands of the Derivative Nucleic Acids Many pairs of target-specific PCR primers/adapters (FIG. 1) are used for the multiplex amplification of many target sequences in a sample. Each of the PCR primers includes the following elements:

1) Target-specific sequences, X, at the 3' ends (Xf and Xr in FIG. 2);
2) Two universal primer sequences (Uf and Ur) at the 5' ends that are common to all the pairs of PCR primers used in an assay;
3) The sequence for a Type IIS restriction endonuclease (R);
4) One or two generic capture tag sequences (T1 and T2) at internal positions in the primers and at specific positions relative to the Type IIS restriction endonuclease recognition sites, such that a double stranded DNA molecule containing these sequences will be cleaved adjacent to the tag sequence leaving the tag sequence in a single-stranded overhang.

Figure 2:
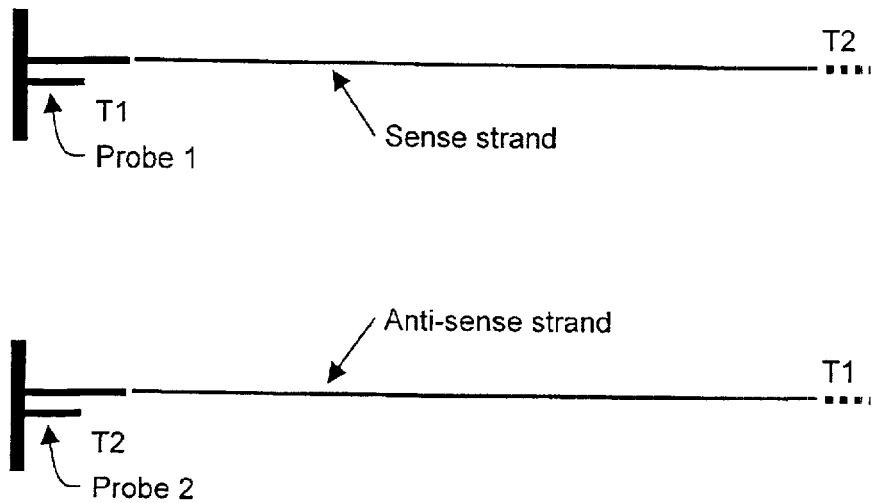
FIG. 2 is an illustration of the protocol for multiplex PCR with two target-specific primers incorporating universal primer sequences, Type IIS restriction sites and generic capture tags, followed by capture of one or both target strands of the derivative nucleic acids.

The protocol is illustrated in FIG. 2. PCR is performed in two phases with the greatest amplification accomplished in the second phase by universal primers complementary to Uf and Ur. (see e.g., Brownie et al, *Nucleic Acids Research* 25:3235, 1997; U.S. Pat. No. 5,858,989, Jeffreys et al; Favis et al, *Nature Biotechnology* 18:561, 2000).

The products are digested with a Type IIS restriction endonuclease to leave the tag sequences in single-stranded overhangs on the ends of the fragments, which products are called derivative nucleic acids. The generic tags are complementary to overhangs on partially duplex probes and hybridize to them. Ligation to the partially duplex probes followed by stringent washing results in the covalent capture of single-stranded DNA containing the sequence to be analyzed. Both strands of the target may be captured on separate array elements if T1 and T2 are different sequences. A polymorphism may be analyzed by primer extension, for example. Polymorphisms can be analyzed in both strands simultaneously on a set of positionally distinguishable partially duplex probes.

EXAMPLE 2

Target-Dependent Ligation and PCR Amplification of Contiguous Probes Incorporating Universal Primer Sequences, Type IIS Restriction Sites and Generic Capture tags, followed by Capture of One or Both Strands of the Derivative Nucleic Acids Many pairs of target-specific PCR probe/primers (FIG. 3) are hybridized and ligated to different target sites in the nucleic acid sample. Each of the probe/primers includes the following elements (FIG. 3):

1) Target-specific sequences at the 3' end (X3' and X 5', respectively) which are complementary to contiguous sequences of the targets and which can be enzymatically ligated if, and only if, the probe sequences match the target sequence (e.g., the position marked "SNP") at the termini;

2) Two universal primer sequences (Uf and Ur) that are common to all the pairs of probes used in an assay;

3) The sequence for a Type IIS restriction endonuclease (R);

4) A capture tag sequence (T1 or T2 on the 5' and 3' probe/primers, respectively) at internal positions and at specific positions relative to the Type IIS restriction endonuclease recognition site, such that a double stranded DNA molecule containing these sequences will be cleaved adjacent to the tag sequence leaving the tag sequence in a single-stranded overhang;

5) An optional signal sequence situated between the restriction site and the target-specific sequence (not shown in FIG. 3) that can encode information about the probe such as the identity of the nucleotide at the terminus of the probe. For the scoring of SNPs, one of four generic sequences would be present in the probes to encode one of the four possible bases.

Figure 4:
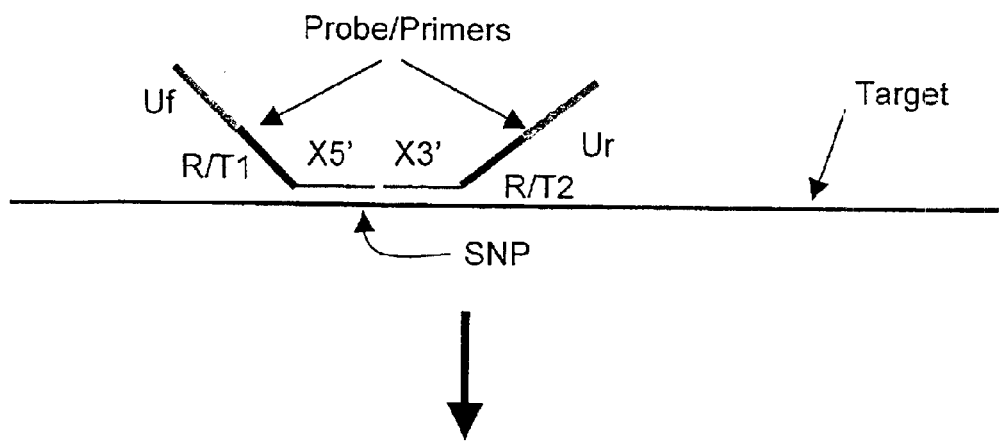
FIG. 4 is an illustration of the protocol for target-dependent ligation and PCR amplification of contiguous probes incorporating universal primer sequences, Type US restriction sites and generic capture tags, followed by capture of one or both strands of the derivative nucleic acids.

The protocol is illustrated in FIG. 4. Ligated probe/primers are amplified by PCR using universal primer pairs complementary to Uf and Ur (common to all the circularizable probes used to analyze targets in a sample) to produce double stranded products (see e.g., Zhang, et al., *Gene* 211:277 (1998); U.S. Pat. No. 5,876,924).

The resulting amplification products are digested with a Type IIS restriction enzyme which leaves the tag sequences (initially positioned internally in the circularizable probe) on single stranded overhangs on the products of the digestion. These products, called derivative nucleic acids, are then captured and sorted on partially duplex probes. Both strands of the target may be captured on separate array elements if T1 and T2 are different sequences. A polymorphism may be analyzed by primer extension, for example. Polymorphisms can be analyzed in both strands simultaneously on a set of positionally distinguishable partially duplex probes.

The presence of specific sequences in target nucleic acids in the sample may be deduced by the presence of derivative nucleic acids on specific partially duplex probes. Two alternative methods may be used (in this or other methods described herein) to analyze target sequences for specific nucleotides at polymorphic sites (SNPs):

1) At least two different types of one of the probe/primers are prepared with different nucleotides at the site of ligation (complementary to the site of a SNP) and with different signal sequences that encode the identity of the nucleotide. Only the probe molecules that are complementary to the target sequence will be ligated and amplified (Zhang, et al., *Gene* 211:277 (1998); U.S. Pat. No. 5,876,924). All of the allele-specific probes for a SNP (i.e., two probes for a biallelic SNP) contain the same capture tag sequence, so all (both for a biallelic SNP) of the resulting derivative nucleic acids are captured by the same partially duplex probe. The allele(s) of the polymorphism is determined by detection the signal sequence with generic hybridization probes complementary to the signal sequences in the derivative nucleic acids. For a biallelic SNPs two generic hybridization probes labeled with distinguishable fluorophors will reveal the allele status of the SNP.

2) Probe/primers are prepared with degenerate nucleotides at the ligation site (complementary to the site of a SNP). Only the probe molecules that are complementary to the target sequence will be ligated and amplified. The resulting derivative nucleic acids are captured on partially duplex probes, and the allele status of the target is determined by a variety of means, such as primer extension reactions.

EXAMPLE 3

Figure 5:
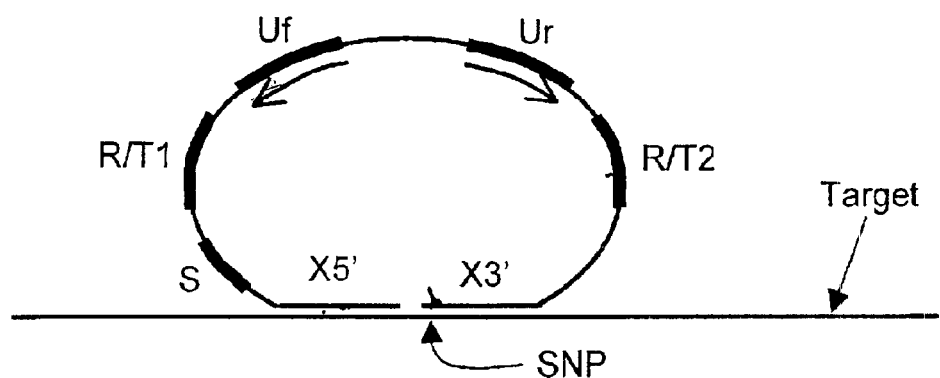
FIG. 5 is a diagram of the elements of circularizable probes containing universal primer sequences, Type IIS restriction sites and generic capture tags that can be used for target-dependent ligation and amplification, followed by capture of one or both strands of the derivative nucleic acids.

Target-Dependent Ligation and Amplification of Circularizable Probes containing Universal Primer Sequences, Type IIS Restriction Sites and Generic Capture Tags, followed by Capture of One or Both Strands of the Derivative Nucleic Acids Many different circularizable probes are hybridized and ligated to different target sites in the nucleic acid sample. Each of the circularizable probes includes the following elements (FIG. 5):

1) Target-specific sequences at the 3' and 5' ends (X3' and X 5', respectively) which are complementary to contiguous sequences of the targets and which can be enzymatically ligated if, and only if, the probe sequences match the target sequence (e.g., the position marked "SNP") at the termini;

2) Two universal primer sequences (Uf and Ur) that are common to all the circularizable probes used in an assay;

3) The sequence for a Type IIS restriction endonuclease (R);

4) One or two capture tag sequences (T1 and T2) at internal positions and at specific positions relative to the Type IIS restriction endonuclease recognition sites, such that a double stranded DNA molecule containing these sequences will be cleaved adjacent to the tag sequence leaving the tag sequence in a single-stranded overhang;

5) An optional signal sequence (S) that can encode information about the probe such as the identity of the nucleotide at one of the termini of the probe. For the scoring of SNPs, one of four generic sequences would be present in the probes to encode one of the four possible bases.

Ligated (circularized) probes are amplified using universal primers (common to all the circularizable probes used to analyze targets in a sample) to produce double stranded products (see e.g., Thomas et al., *Arch Pathol Lab Med* 123:1170, 1999; Zhang, et al., *Gene* 211:277 (1998); U.S. Pat. No. 5,876,924). The priming sites are situated in the circularizable probe so that the amplification is ligation dependent (see e.g., Thomas et al., *Arch Pathol Lab Med* 123:1170, 1999; Zhang, et al., *Gene* 211:277 (1998); U.S. Pat. No. 5,876,924), and so that the target dependent sequence, the type II S restriction site, the capture tag sequence and the optional signal sequence are amplified. The direction in which the primers are extended is indicated by the arrows in FIG. 5.

The resulting multimer amplification products are digested with a Type IIS restriction enzyme which leaves the generic tag sequences (initially positioned internally in the circularizable probe) on single stranded overhangs on the products of the digestion. These products, called derivative nucleic acids, are then captured and sorted on partially duplex probes.

The presence of specific sequences in target nucleic acids in the sample may be deduced by the presence of derivative nucleic acids on specific partially duplex probes. Two alternative methods may be used to analyze target sequences for specific nucleotides at polymorphic sites (SNPs):

1) Separate circularizable probes are prepared with different nucleotides at the site of ligation (complementary to the site of a SNP) and with different signal sequences that encode the identity of the nucleotide. Only the probe molecules that are complementary to the target sequence will be ligated and circularized. All of the allele-specific probes for a SNP (i.e., two probes for a biallelic SNP) contain the same capture tag sequence, so all (both for a biallelic SNP) of the resulting derivative nucleic acids are captured by the same partially duplex probe. The allele(s) of the polymorphism is determined by detection the signal sequence with generic hybridization probes complementary to the signal sequences in the derivative nucleic acids. For a biallelic SNPs two generic hybridization probes labeled with distinguishable fluorophors will reveal the allele status of the SNP.

2) Probes are prepared with degenerate nucleotides at the ligation site (complementary to the site of a SNP). Only the probe molecules that are complementary to the target sequence will be ligated and circularized. The resulting derivative nucleic acids are captured on partially duplex probes, and the allele status of the target is determined by a variety of means, such as primer extension reactions.

EXAMPLE 4

Figure 6:
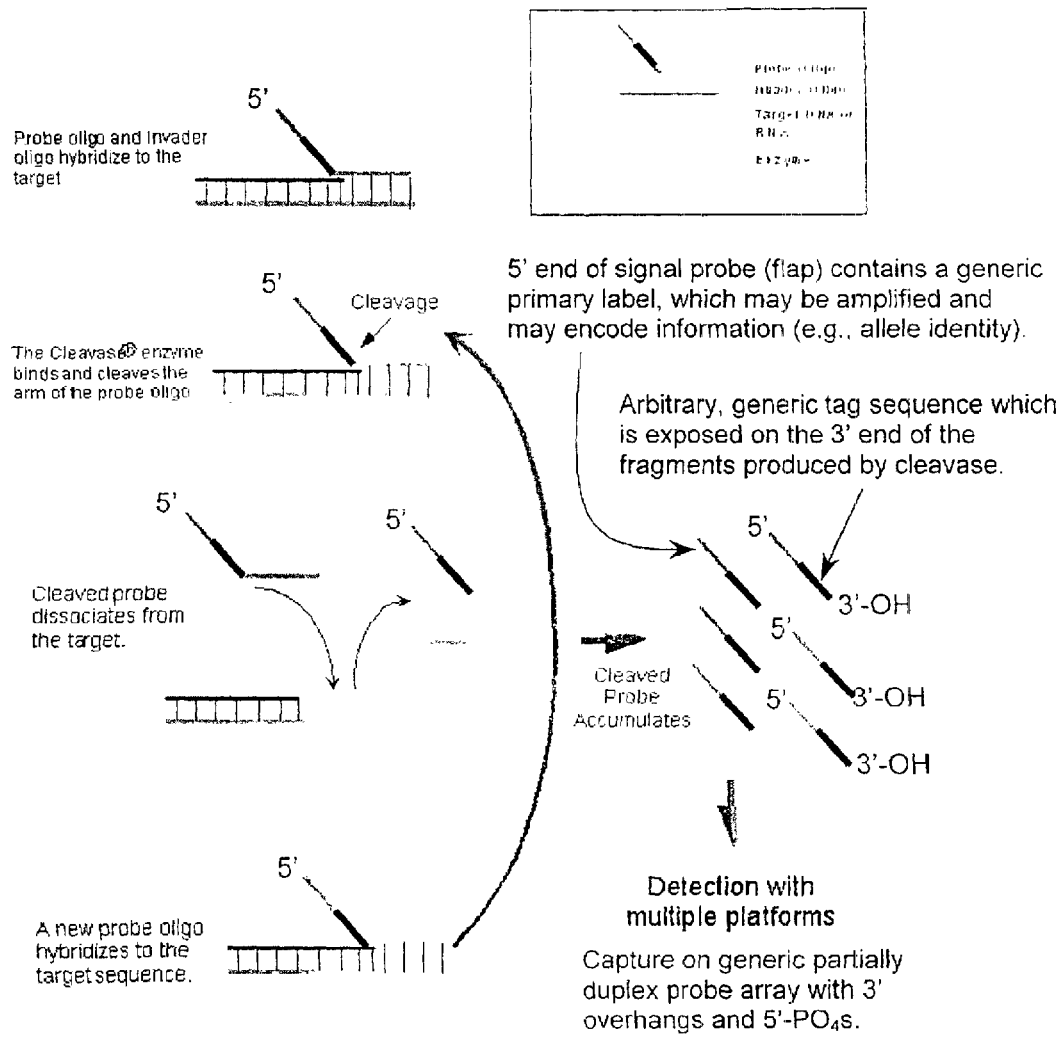
FIG. 6 is an outline of the Cleavase Invader assays (Third Wave Technologies) showing the elements of flap sequences that may be used for capture and detection on partially duplex probes.

Specific Capture and Sorting of Flap Products from Multiplexed Cleavase Invader Assays on partially Duplex Arrays Many different pairs of Invader probes are hybridized to different target sites in the nucleic acid sample. Each pair consists of an invader oligonucleotide which forms a relatively stable hybrid with the target nucleic acid and a signal probe which hybridizes transiently to the target at a position adjacent to the invader probe (see e.g., Ryan et al., *Mol Diagn* 4:135, 1999, Griffin et al., *Proc Natl Acad Sci USA* 96:6301, 1999). Many signal probes cycle on and off the target sequence, and they are cleaved by an endonuclease if and only if the sequence of the signal probe matches the target at the overlap between the signal probe and the invader probe. The signal probe includes the following elements (FIG. 6):

1) A 3' region with sequence complementary to the target;
2) An arbitrary capture tag sequence that is initially positioned internally and that includes at least one target-specific nucleotide that will be present on the 3' terminus of the expected cleavage product;
3) A 5' region which can have an arbitrary signal sequence or a label moiety for detection of the product.

The flap products (derivative oligonucleotides) resulting from a multiplexed invader assay are captured and sorted by different partially duplex probes. The label on the 5' end of the flap-can encode information about the probe that was cleaved such as the identity of the nucleotide in the overlap between the invader probe and the signal probe and hence the allele of a polymorphism. For a biallelic SNPs two generic hybridization probes complementary to the generic signal sequences and labeled with distinguishable fluorophors will reveal the allele status of the SNP. Alternatively, the generic hybridization probes used to detect the captured flaps (derivative oligonucleotides) can serve as generic primer sequences for rolling circle amplification with preformed circle. With this method of detection great signal amplification can be achieved.

REFERENCES

The following references may be useful in the practice of method disclosed herein, all references including patents, applications, and publications, cited in this section, and elsewhere herein, are hereby incorporated by reference.

U.S. Pat. No. 5,858,989, Jeffreys et al.
U.S. Pat. No. 5,422,252, Walker et al.
U.S. Pat. No. 5,876,924, Zhang et al.
U.S. Pat. No. 5,846,717, Brow et al.
U.S. Pat. No. 5,888,780, Dahlberg et al.
U.S. Pat. No. 5,985,557, Prudent et al.
U.S. Pat. No. 5,994,069, Hall et al.
U.S. Pat. No. 6,001,567, Brow et al.
U.S. Pat. No. 5,503,980, Cantor
"Large-Scale Identification, Mapping, and Genotyping of Single-Nucleotide Polymorphisms in the Human Genome", Wang et al., *Science* 280:1077 (1998)
"The elimination of primer-dimer accumulation in PCR", Brownie et al, *Nucleic Acids Research* 25:3235 (1997)
"Universal DNA array detection of small insertions and deletions in BRCA1 and BRAC2", Favis et al, *Nature Biotechnology* 18:561 (2000)
"Amplification of padlock probes for DNA diagnostics by cascade rolling circle amplification or the polymerase chain reaction", Thomas et al., *Arch Pathol Lab Med* 123:1170 (1999)
"Accessing genomic information: alternative to PCR", Isaksson and Landegren, *Curr OpinBiotechnol.* 10:11 (1999)
"Non-PCR-dependent detection of the factor V Leiden mutation from genomic DNA using a homogeneous invader microtiter plate assay", Ryan et al, *Mol Diagn* 4:135 (1999)

"Direct genetic analysis by matrix-assisted laser desorption/ ionization mass spectrometry", Griffin et al., *Proc Natl Acad Sci USA* 96:6301(1999)

"Characterization of single-nucleotide polymorphisms in coding regions of human genes", Cargill et al., *Nature Genetics* 22: 231 (1999)

"Enhanced DNA sequencing by hybridization", Broude et al., *Proc. Natl. Acad. Sci.* 91: 3072 (1994)

"Mutation detection by ligation to complete n-mer DNA arrays", Gunderson et al., *Genome Research* 8:1142 (1998)

"Determining the influence of structure on hybridization using oligonucleotide arrays", Mir and Southern, *Nature Biotechnology* 17:788 (1999)

"Minisequencing: a specific tool for DNA analysis and diagnostics on oligonucleotide arrays", Pastinen, et al., *Genome Research* 7:606 (1997)

"Amplification of target-specific, ligation dependent circular probe", Zhang, et al., *Gene* 211:277 (1998)

Other embodiments are within the following claims.

What is claimed is:

1. A method of analyzing a sample of nucleic acids, the method comprising:

providing a plurality of probe molecules wherein the plurality comprises at least one probe molecule for each target nucleic acid sequence to be analyzed, the probe molecule comprising a region of sequence substantially complementary to a sequence in the target nucleic acid sequence and an internal capture tag sequence that is internal to a nucleic acid strand of said probe molecule;

contacting the plurality of probe molecules to a sample of nucleic acids under conditions that allow a set of probe molecules for which a complementary sequence is present among the nucleic acids of the sample, to hybridize to the respective complementary sequence;

cleaving the probes molecules of the set, wherein the cleavage is specific for the probe molecules that hybridize to nucleic acids of the sample and the cleavage positions the capture tag sequence of each cleaved probe molecule at a terminus of the cleaved probe molecule; and detecting one or more of the cleaved probes by hybridizing the tag sequences to capture probes disposed on a substrate, thereby analyzing the sample of nucleic acids.

2. The method of claim 1 herein each probe molecule comprises a Type IIS restriction endonuclease recognition site positioned such that cleavage of the recognition site in a double studded DNA into which the probe molecule is incorporated generates a nucleic acid having a single-stranded overhang that includes the tag sequence.

3. The method of claim 1, wherein the cleaving positions the capture tag sequence of each cleaved probe molecule in a single-stranded overhang.

4. The method of claim 3, wherein detecting comprises hybridizing capture tag sequences of the one or more cleaved probes to a plurality of capture probes.

5. The method of claim 4, where in each capture probe of the plurality of capture probes comprises a double stranded region and a single stranded region.

6. The method of claim 5, wherein the 3' end of the single stranded region is extendable.

7. The method of claim 5, wherein each capture probe of the plurality of capture probes forms a hairpin structure.

8. The method of claim 5, wherein each capture probe of the plurality of capture probes comprises a chemical moiety that allows for immobilization.

9. The method of claim 1 wherein detecting comprises hybridizing capture tag sequences of the one or more cleaved probes to a plurality of capture probes.

10. The method of claim 9, wherein the detecting comprises an enzyme mediated reaction.

11. The method of 10 wherein a derivative nucleic acid is a substrate or template for the enzyme mediated reaction.

12. The method of claim 10 wherein a capture probe is a substrate or template for the enzyme mediated reaction.

13. The method of claim 1 wherein the internal capture tag sequence of each probe molecule of the plurality of molecules is between 4 and 20 nucleotides in length.

14. The method of claim 1 wherein the internal capture tag sequence of each probe molecule of the plurality of probe molecules is 4 and 8 nucleotides in length.

15. The method of claim 1 wherein the internal capture tag sequence of each probe molecule of the plurality of probe molecules is unique.

16. The method of claim 1 further comprising ligating capture tag sequences of the one or more cleaved probes to capture probes of the plurality of capture probes.

17. The method of claim 1 further comprising, prior to the cleaving, extending probe molecules that hybridize to nucleic acids of the sample.

18. The method of claim 1 wherein the cleaving comprises cleavage by a Type IIS restriction endonuclease.

19. The method of claim 1 wherein the cleaving comprises cleavage by a flap endonuclease.

* * * * *